US008454609B2

(12) United States Patent
Petit et al.

(10) Patent No.: US 8,454,609 B2
(45) Date of Patent: Jun. 4, 2013

(54) ACETABULAR REAMER

(75) Inventors: Yvan Petit, St-Mathieu de Beloeil (CA); Julio Fernandes, Brossard (CA); Jean-Sebastien Merette, Mont St-Hilaire (CA); Mathieu Dansereau, Montréal (CA); Victor Songmene, Ottawa (CA); Mathieu Carrier, Montreal (CA)

(73) Assignee: École de Technologie Supérieure, Montreal (CA)

( * ) Notice: Subject to any disclaimer, the term of this patent is extended or adjusted under 35 U.S.C. 154(b) by 404 days.

(21) Appl. No.: 12/733,294

(22) PCT Filed: Aug. 21, 2008

(86) PCT No.: PCT/CA2008/001525
§ 371 (c)(1),
(2), (4) Date: Jun. 9, 2010

(87) PCT Pub. No.: WO2009/023972
PCT Pub. Date: Feb. 26, 2009

(65) Prior Publication Data
US 2010/0286697 A1  Nov. 11, 2010

Related U.S. Application Data

(60) Provisional application No. 60/935,603, filed on Aug. 21, 2007.

(51) Int. Cl.
*A61B 17/00* (2006.01)
(52) U.S. Cl.
USPC .......................................................... 606/81
(58) Field of Classification Search
USPC .............. 606/79–85, 167–189; 433/144, 145, 433/153, 154; 408/153, 158, 161, 168, 169, 408/170, 173
See application file for complete search history.

(56) References Cited

U.S. PATENT DOCUMENTS

| | | | |
|---|---|---|---|
| 3,702,611 A | 11/1972 | Fishbein |
| 4,131,116 A | 12/1978 | Hedrick |
| 4,271,849 A | 6/1981 | Rehder |
| 4,611,587 A | 9/1986 | Powlan |
| 4,621,637 A | 11/1986 | Fishbein |
| 6,283,971 B1 | 9/2001 | Temeles |
| 6,918,914 B2 | 7/2005 | Bauer |
| 2004/0167528 A1 | 8/2004 | Schantz |
| 2006/0025774 A1 | 2/2006 | Fishbein et al. |
| 2006/0149270 A1 | 7/2006 | Myers |
| 2006/0217730 A1 | 9/2006 | Termanini |
| 2006/0264958 A1 | 11/2006 | Ezzedine |
| 2007/0016211 A1 | 1/2007 | Botimer |
| 2007/0016212 A1 | 1/2007 | Wolford |
| 2007/0112435 A1 | 5/2007 | Tarabishy |

*Primary Examiner* — Todd Manahan
*Assistant Examiner* — Eric S Gibson

(57) ABSTRACT

An acetabular reamer comprising: a body defining a rotation axis about which the acetabular reamer is rotatable; a reaming element movable between a reaming element inner position and a reaming element outer position relative to the body; an actuator for moving the reaming element between the reaming element inner and outer positions; and a reaming element lock configurable between a locked configuration and an unlocked configuration. In the unlocked configuration, the reaming element is freely movable by the actuator between the reaming element inner and outer positions. In the locked configuration, the reaming element lock prevents the reaming element from moving relative to the body. In use, when the reaming element lock is in the locked configuration and reaction forces are exerted onto the reaming element, a larger portion of the reaction forces is transmitted to the body than to the actuator.

17 Claims, 15 Drawing Sheets

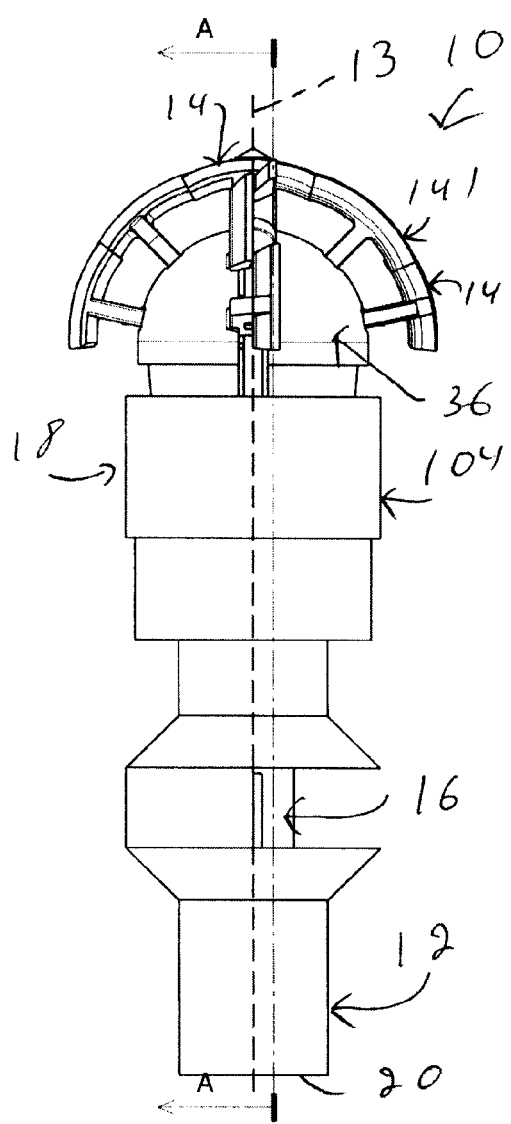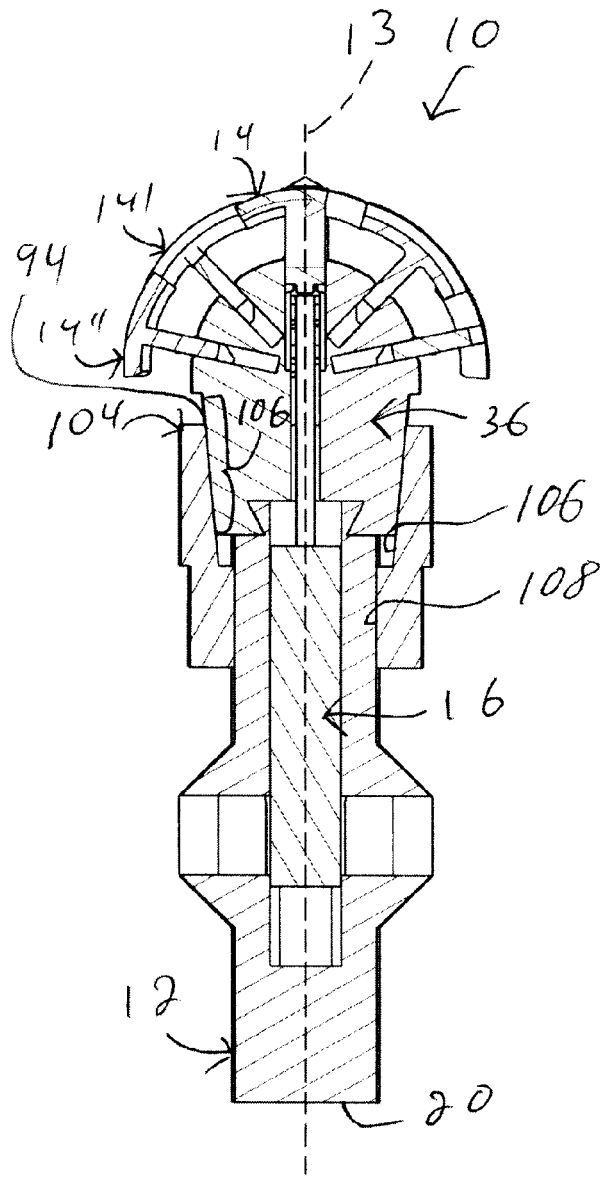

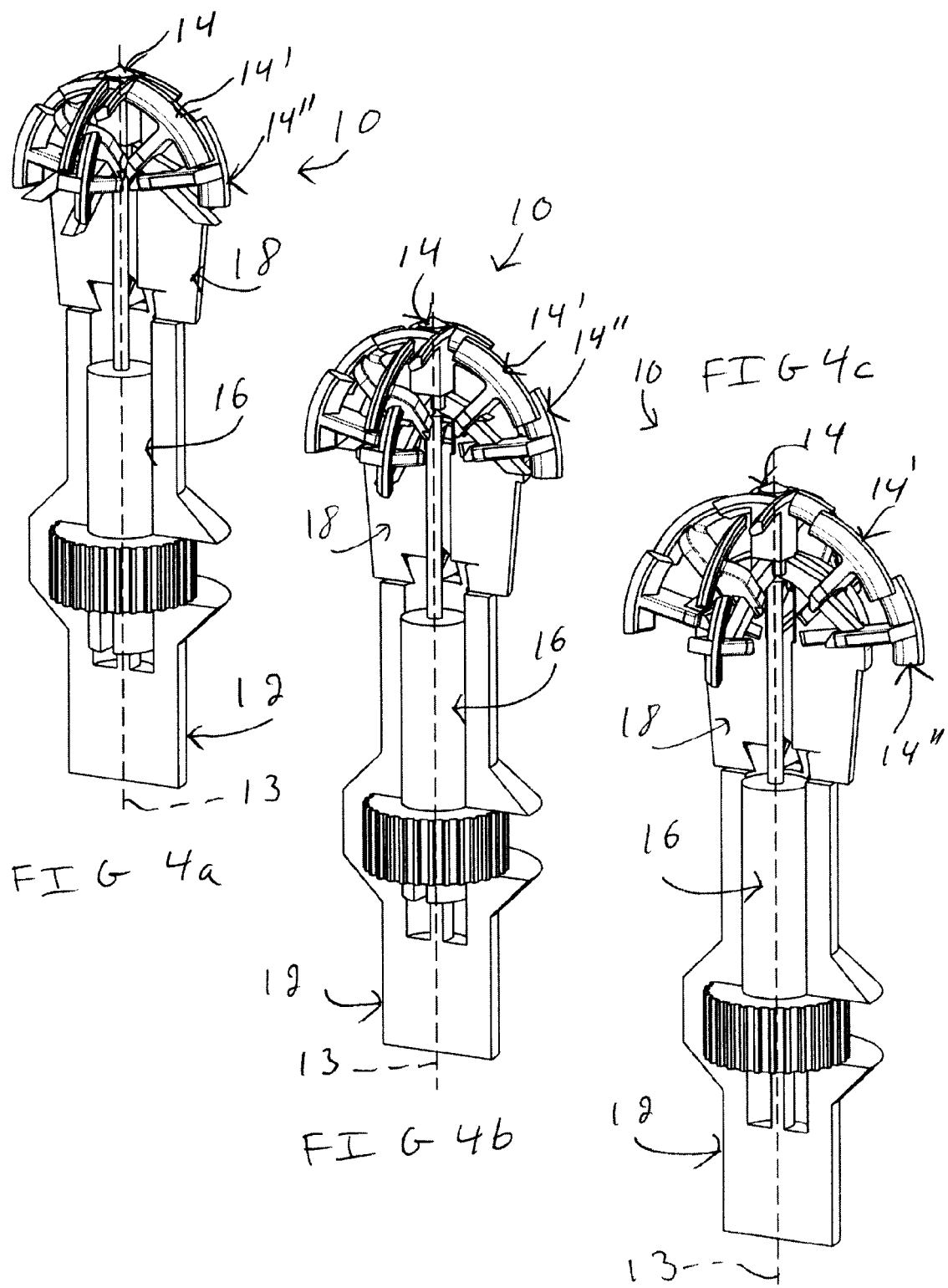

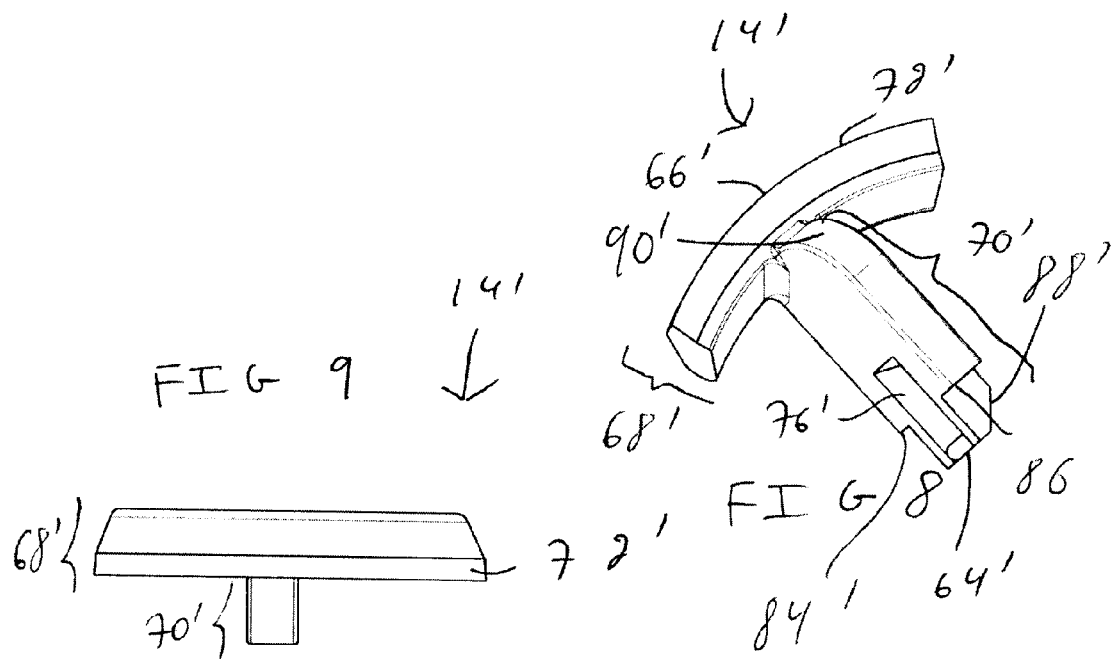
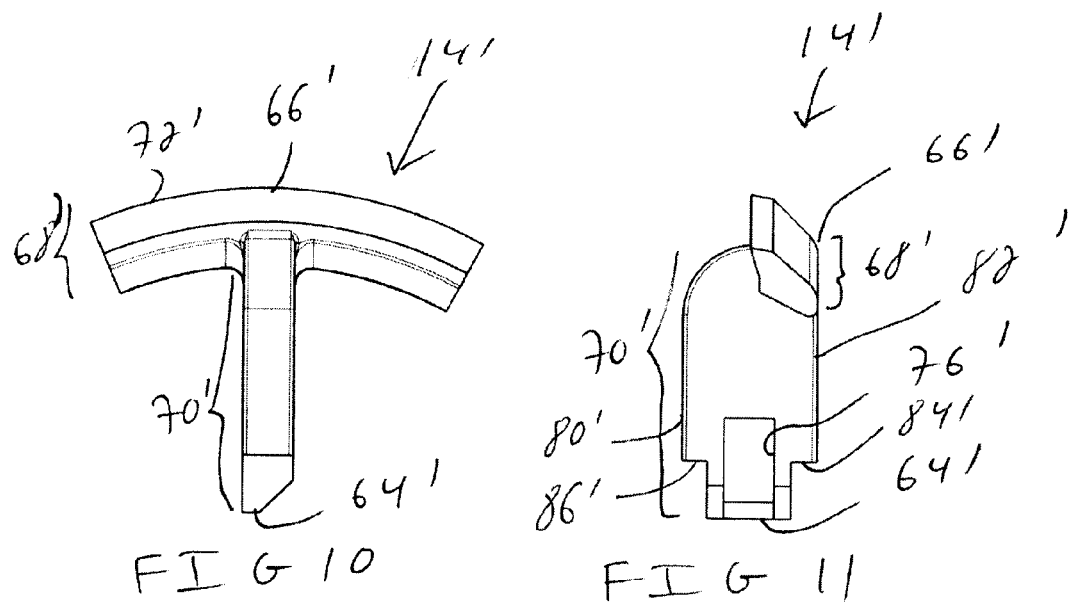

ACETABULAR REAMER

The present application is a National Stage Entry of PCT Application Serial Number PCT/CA2008/001525 filed on Aug. 21, 2008, which application claims priority from U.S. Provisional Patent Application Ser. No. 60/935,603 filed on Aug. 21, 2007.

FIELD OF THE INVENTION

The present invention relates to the art of surgical devices. More specifically, the present invention is concerned with an acetabular reamer.

BACKGROUND

Acetabular reamers are used in hip replacement surgery to prepare the acetabulum of the hip of a patient before the attachment of an acetabular cup thereto. In such surgeries, there is typically a need to prepare the acetabulum so that a substantially spherical cap-shaped surface is provided to receive a substantially hemispherical acetabular cup. To that effect, a surgeon typically uses a reamer including a substantially hemispherical reaming element in which asperities are formed. The reaming element is longitudinally mounted to the distal end of an axle and the axle is attached to a rotary power tool such as, for example, a drill. The drill rotates the axle about the longitudinal axis of the axle, thereby rotating the reaming element to allow reaming of the acetabulum.

Hip replacement surgery is performed typically after having performed a relatively small incision in a patient, the incision being used for introducing and removing surgical instruments and tissue debris therethrough. Each time an instrument is inserted in the patient, or removed therefrom, there is a risk that soft tissues adjacent the incision become damaged by this action.

In the above-described reaming method, the surgeon typically needs to remove and re-insert repeatedly the acetabular reamer to change the reaming element by a reaming element having a slightly larger diameter in each successive iteration. This allows the surgeon to gradually ream the acetabulum to a desired shape and dimension.

In turn, this requires that many reaming elements be brought into an operating room, which results in relatively large sterilizing costs. Furthermore, the repetitive insertion and removal of the acetabular reamer from the patient is time-consuming and may cause injuries to soft tissues adjacent the incision.

Another problem of many conventional acetabular reamers is that the reaming element typically includes asperities that are spaced apart from each other. These asperities therefore do not produce directly a relatively smooth surface and the surgeon needs to move the acetabular reamer in a substantially ball-joint-like motion inside the patient to achieve a substantially uniform surface suitable for the attachment of the acetabular cup thereto. Since the surgeon typically does not see the result of this operation, there is always a risk that the resulting surface is not smooth enough and results in sub-optimal implementation of the acetabular cup. Another disadvantage of this motion is that, once again, it creates a risk of injuring soft tissues inside the patient.

A few acetabular reamers having variable dimensions have been previously described. For example, U.S. Pat. No. 6,918,914 issued on Jul. 19, 2005 to Bauer describes an acetabular reamer including arcuately-shaped segments that are extendable and retractable about a center point to create variably dimensioned recesses in an acetabular region. However, in this acetabular reamer, when the arcuately-shaped segments are moved away from the central location, the arcuately-shaped segments become spaced apart from each other, which therefore create gaps therebetween. In turn, this requires that the surgeon operate the acetabular reamer substantially in the ball-joint-like motion described hereinabove. Also, when the acetabular reamer is used to ream the acetabulum, mechanical forces transmitted by the arcuately-shaped segments to the remainder of the acetabular reamer are relatively large, which therefore requires that the mechanism used to extend and retract the arcuately-shaped segments be relatively sturdy. This leads to a restriction to a relatively small number of the number of arcuately-shaped segments that can be provided because of size limitations present in such reamers. Also, the surface formed by the arcuately-shaped segments is spherical at only one single overall diameter. For other dimensions, the reamed surface will deviate from a perfect sphere, and since the number of segments is relatively small, such deviations are relatively large in the acetabular reamer proposed by Bauer.

A US Patent Application filed by Termanini and published under the publication number 2006/0217730 on Sep. 28, 2006 describes another acetabular reamer including deployable segments deployable by a deployment mechanism. A disadvantage of this acetabular reamer resides in the presence of pivots in the deployment mechanism, the pivots being load-bearing when the acetabular reamer is in use. Such pivots are relatively fragile and introduce failure points in the design of this acetabular reamer. Also, manufacturing imprecisions in the pivots can lead to the creation of vibrations when the acetabular reamer is in use. Furthermore, the pivots form a structure that is relatively difficult to clean and sterilize.

Another extendable acetabular reaming system has been described by Temeles in U.S. Pat. No. 6,283,971 issued Sep. 4, 2001. In this reamer, a reamer head has a convex forward surface attached to a plate that defines an interior space therebetween. The forward space includes apertures extending therethrough and the base plate includes a central aperture over which a flexible bladder is mounted within the interior space. The reaming system includes cutting blades mounted to the bladder and positioned so as to correspond with respective apertures. The bladder is inflatable so as to extend the blades through the apertures to a variable extent. Once again, in this system, there are gaps between the blades, which will therefore not alleviate one of the problems mentioned hereinabove. Also, any gap between the blades and the apertures will create vibration in the acetabular reamer when the acetabular reamer is used to ream the acetabulum.

Accordingly, there is a need in the industry to provide an improved acetabular reamer. An object of the present invention is therefore to provide such an acetabular reamer.

SUMMARY OF THE INVENTION

In a broad aspect, the invention provides an acetabular reamer for reaming an acetabulum, reaction forces being exerted onto the acetabular reamer by the acetabulum when the acetabulum is reamed, the acetabular reamer comprising: a body, the body defining a rotation axis about which the acetabular reamer is rotatable; a reaming element operatively coupled to the body so as to be movable between a reaming element inner position and a reaming element outer position relatively thereto, the reaming element being positioned further away from the rotation axis in the reaming element outer position than in the reaming element inner position; an actuator operatively coupled to the reaming element for moving the reaming element between the reaming element inner and outer positions; and a reaming element lock configurable between a locked configuration and an unlocked configuration, the reaming element lock being operatively coupled to the reaming element in a manner such that when the reaming element lock is in the unlocked configuration, the reaming element is substantially freely movable by the actuator between the reaming element inner and outer positions, and when the reaming element lock is in the locked configuration, the reaming element lock substantially prevents the reaming element from moving relatively to the body; the reaming element lock being configured, sized and operatively coupled to the reaming element and the body in a manner such that when the reaming element lock is in the locked configuration and the reaction forces are exerted onto the reaming element, a larger portion of the reaction forces is transmitted to the body than to the actuator.

Advantageously, in some embodiments of the invention, the proposed acetabular reamer includes a relatively large number of reaming elements as the actuator may have a relatively complex configuration while fitting within the relatively small inner space defined by the reaming elements. Indeed, the relatively large reaction forces exerted onto the acetabular reamer when in use are transmitted to the body not through the actuator, but through the reaming element lock. Since the reaming element lock may be configured so as to be relatively sturdy while remaining confined within the surface defined by the reaming elements, the proposed acetabular reamer is relatively sturdy even when including a relatively large number of reaming elements and a relatively fragile actuator.

Furthermore, in some embodiments of the invention, the reaming elements each define a respective reaming surface, the reaming surfaces being arranged along the meridians of a substantially spherical-cap-shaped surface.

Advantageously, in some embodiments of the invention, the reaming surfaces are arranged such that there is a circumferential overlap between the reaming surfaces of the reaming elements extending along each meridian, which, therefore, eliminates gaps through which no reaming occurs when the acetabular reamer is rotated about the rotation axis.

The proposed acetabular reamer is further ergonomic to use and relatively easily manufacturable using known materials and techniques.

The use of the proposed acetabular reamer allows an intended user to use only a relatively small number of components to ream cavities having various dimensions.

In some embodiments of the invention, the proposed acetabular reamer is relatively easily dismantled into individual components that are each relatively easily cleanable and sterilizable.

Another advantage of having an acetabular reamer including many reaming elements resides in that the use of many reaming elements allows for reaming a cavity that deviates only slightly from the surface of a perfect sphere.

Other objects, advantages and features of the present invention will become more apparent upon reading of the following non-restrictive description of preferred embodiments thereof, given by way of example only and in relation with the following Figures.

BRIEF DESCRIPTION OF THE DRAWINGS

FIG. 2, in a side elevation view, illustrates the acetabular reamer shown in FIG. 1;

FIG. 3, in a side cross-sectional view along the line A-A shown in FIG. 2, illustrates the acetabular reamer shown in FIGS. 1 and 2;

FIG. 4a, in a perspective view with parts and portions removed, illustrates the acetabular reamer shown in FIGS. 1 to 3, the acetabular reamer being shown in a retracted configuration;

FIG. 4b, in a perspective view with parts and portions removed, illustrates the acetabular reamer shown in FIGS. 1 to 4a, the acetabular reamer being shown in an intermediate configuration;

FIG. 4c, in a perspective view with parts and portions removed, illustrates the acetabular reamer shown in FIGS. 1 to 4b, the acetabular reamer being shown in an expanded configuration;

FIG. 8, in a perspective view, illustrates a reaming element of a second type included in the acetabular reamer shown in FIGS. 1 to 7;

FIG. 9, in a top plan view, illustrates the reaming element of the second type shown in FIG. 8;

FIG. 10, in a side elevation view, illustrates the reaming element of the second type shown in FIGS. 8 and 9;

FIG. 11, in a front elevation view, illustrates the reaming element of the second type shown in FIGS. 8 to 10;

DETAILED DESCRIPTION

Figure 1:
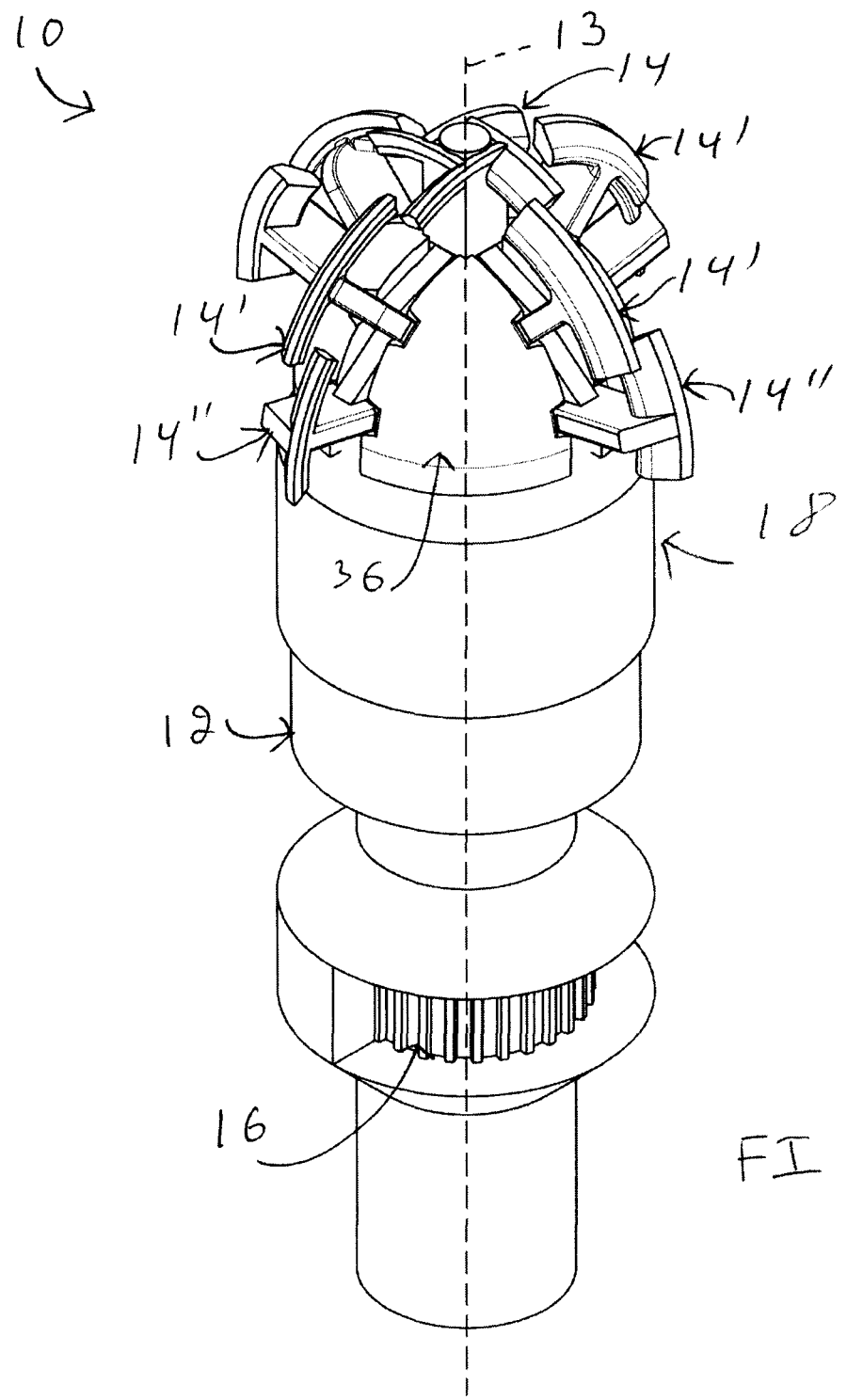
FIG. 1, in a perspective view, illustrates an acetabular reamer in accordance with an embodiment of the present invention.

Referring to FIG. 1, there is shown an acetabular reamer 10 usable by an intended user (not shown in the drawings) for reaming an acetabulum (not shown in the drawings). The acetabular reamer 10 includes a body 12, the body 12 defining a rotation axis 13 about which the acetabular reamer 10 is rotatable by the intended user.

The acetabular reamer 10 includes at least one reaming element 14, 14', 14". As described in further details hereinbelow, the acetabular reamer 10 shown in the drawings includes a reaming element of a first type 14, four reaming elements of a second type 14' and four reaming elements of a third type 14". However, in alternative embodiments of the invention, the acetabular reamer 10 includes any suitable number of reaming elements 14, 14' and 14" and any suitable number of types of reaming elements 14, 14', 14".

Figures 5A, 5B:
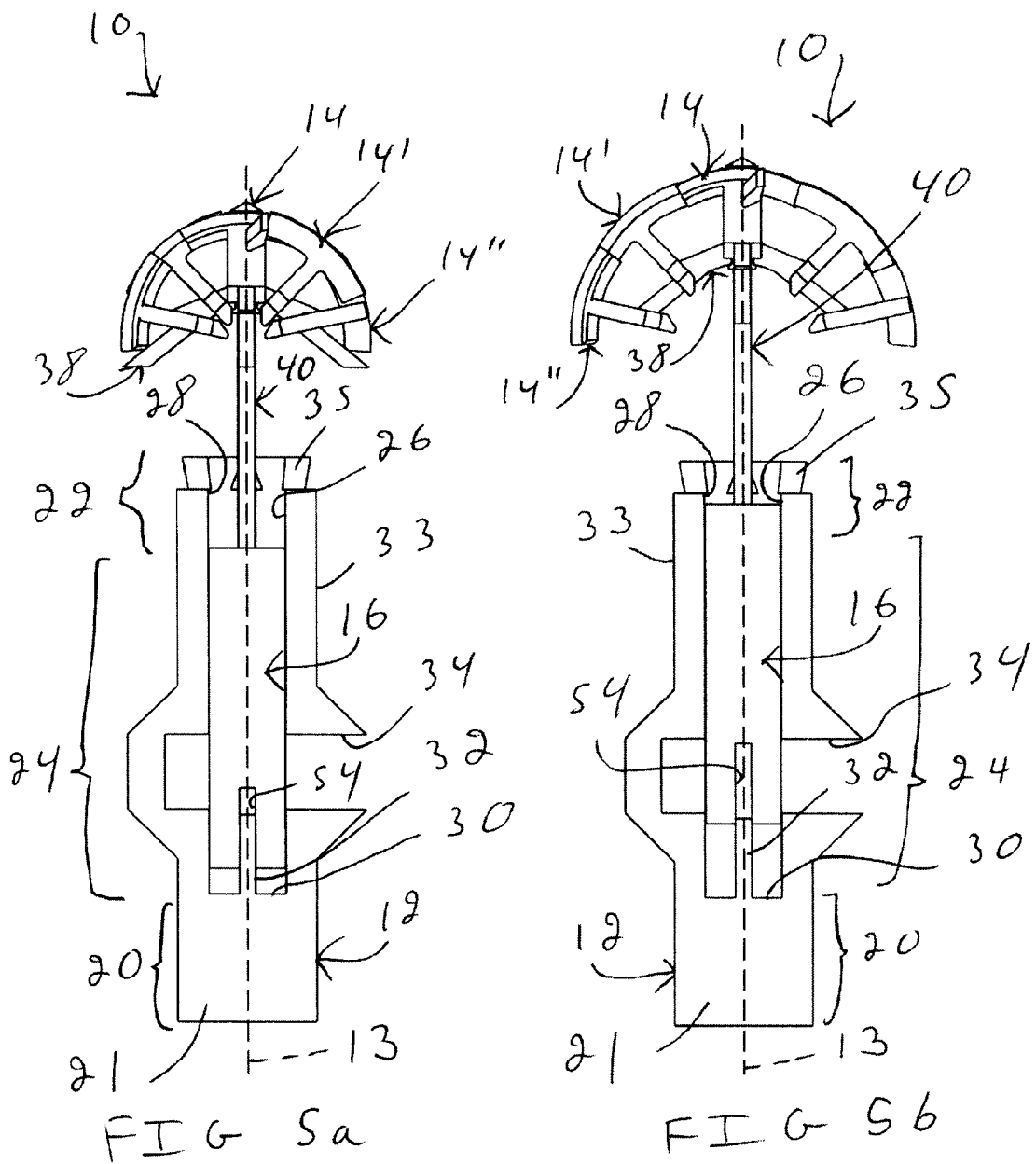
FIG. 5a, in a side elevation view with parts removed, illustrates the acetabular reamer shown in FIGS. 1 to 4c, the acetabular reamer being shown in the retracted configuration.
FIG. 5b, in a side elevation view with parts removed, illustrates the acetabular reamer shown in FIGS. 1 to 5a, the acetabular reamer being shown in the expanded configuration.

Each reaming element 14, 14' 14" is operatively coupled to the body 12 so as to be movable between a respective reaming element inner position shown, for example, in FIGS. 4a and 5a, and a respective reaming element outer position shown, for example, in FIGS. 4c and 5b, relatively to the body 12. Also, as illustrated in FIG. 4b, each reaming element 14, 14', 14" may be moved at a respective reaming element intermediate position located intermediate the reaming element inner and outer positions. Each reaming element 14' and 14" is positioned further away from the rotation axis 13 in the reaming element outer position than in the reaming element inner position, except for the reaming element 14 which moves substantially longitudinally away from the body 12 when moving from the reaming element inner position to the reaming element outer position.

As seen for example in FIGS. 4a to 5b, the acetabular reamer 10 also includes an actuator 16, the actuator 16 being operatively coupled to the body 12 and to the reaming elements 14, 14', 14" so as to allow the intended user (not shown in the drawings) to move the reaming elements 14, 14' 14" between their respective reaming element inner and outer positions.

Figure 22A:
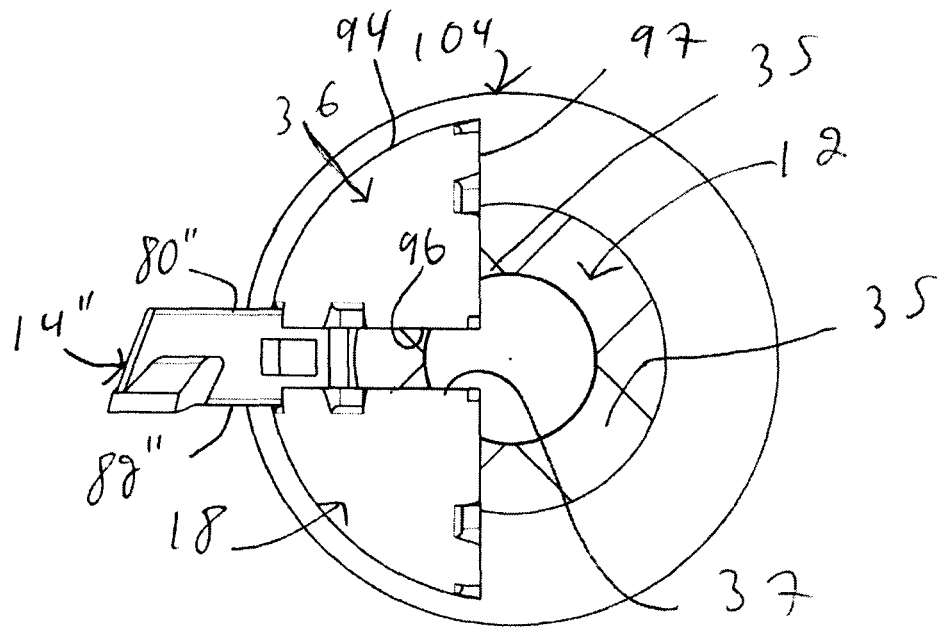
FIG. 22a, in a top elevation view with parts removed, illustrates the acetabular reamer shown in FIGS. 1 to 7, the acetabular reamer being shown with the locking component thereof in a locked configuration.
Figure 22B:
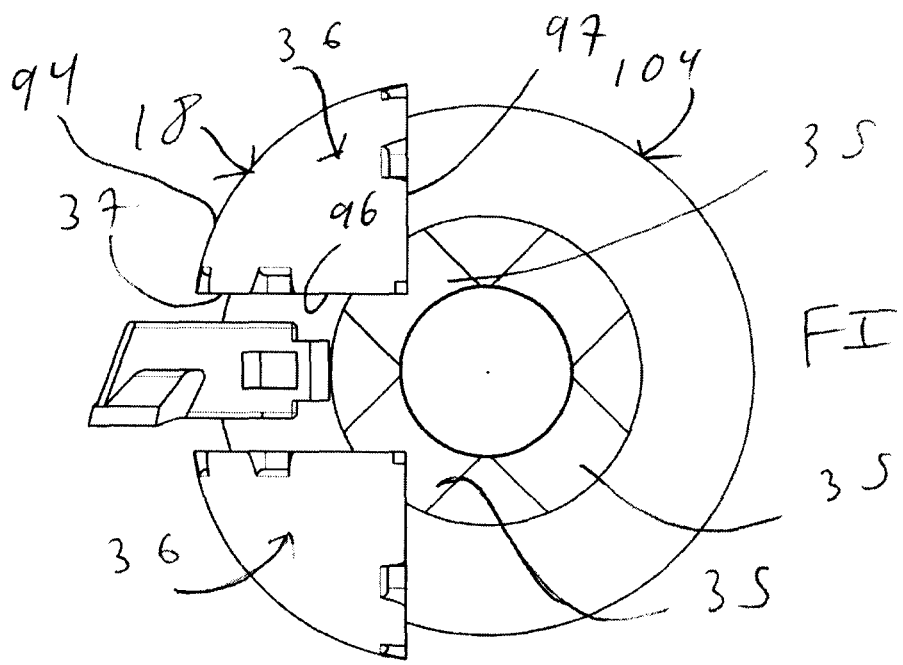
FIG. 22b, in a top elevation view with parts removed, illustrates the acetabular reamer shown in FIGS. 1 to 7, the acetabular reamer being shown with the locking component thereof in an unlocked configuration.

A reaming element lock 18, shown for example in FIGS. 2, 22a and 22b, is operatively coupled to the body 12 and to the reaming elements 14, 14' 14" so as to be configurable between a locked configuration, shown in FIG. 22a, and an unlocked configuration, shown in FIG. 22b. In the unlocked configuration, the reaming elements 14, 14', 14" are substantially free to move under the action of the actuator 16 between the reaming element inner and outer positions. In the locked configuration, the reaming element lock 18 substantially prevents the reaming elements 14, 14', 14" from moving relatively to the body 12.

Typically, the reaming element lock 18 is configured, sized and operatively coupled to the reaming elements 14, 14' and 14" and to the body 12 in a manner such that when the reaming element lock 18 is in the locked configuration and reaction forces are exerted onto the reaming elements 14, 14' and 14", for example when the acetabular reamer 10 is used to ream the acetabulum (not shown in the drawings), a larger portion of the reaction forces is transmitted to the body 12 than to the actuator 16. Typically, substantially all the reaction forces are transmitted directly to the body 12 by the reaming element lock 18.

Referring to FIGS. 5a and 5b, the body 12 defines a body proximal end section 20, a substantially opposed body distal end section 22 and a body intermediate section 24 extending therebetween. The body proximal end section 20 is attachable to a rotary power tool (not shown in the drawings) usable for rotating the acetabular reamer 10 about the rotation axis 13. For example, the body proximal end section 20 defines a power tool attachment 21, which may in some embodiments take the form of a substantially elongated shaft, is attachable to a power drill (not shown in the drawings) in a conventional manner.

The body 12 defines a body recess 26 extending from the body distal end section 22 substantially longitudinally into the body 12 towards the body proximal end section 20. The body recess 26 is provided for receiving the actuator 16 and therefore allows mounting the actuator 16 to the body 12. The body recess 26 defines a recess aperture 28 in the body distal end section 22 leading into the body recess 26. The actuator 16 extends substantially longitudinally outwardly from the body recess 26 through the recess aperture 28 and is mounted thereinto so as to be longitudinally movable relatively thereto. The body recess 26 defines a recess end wall 30 located substantially opposed to the recess aperture 28 and a recess protrusion 32 extending substantially longitudinally from the recess end wall 30 towards the recess aperture 28.

The body 12 defines a body outer surface 33. An access aperture 34 extends substantially radially between the body outer surface 33 and the body recess 26 and allows access to the actuator 16 so as to operate the actuator 16 to move the reaming elements 14, 14', 14".

The body distal end section 22 defines locking component attachments 35 for attaching the reaming element lock 18 to the body 12. For example, the locking component attachments 35 take the form of protrusions formed into the body distal end section 22, the protrusions tapering both in a direction leading towards the body proximal end section 20 and in direction leading towards the body recess 26. For example, the locking component attachments 35 have a substantially frustro-pyramidal configuration.

Still referring to FIGS. 5a and 5b, the actuator 16 includes a reaming element mounting portion 38 for mounting the reaming elements 14, 14' and 14" thereto. A mounting portion support 40 is mounted to the body 12 and supports the reaming element mounting portion 38. The mounting portion support 40 is mounted to the body 12 so as to be substantially longitudinally movable therealong and allows mounting of the actuator 16 to the body 12. For example, the mounting portion support 40 is substantially elongated and extends substantially longitudinally from the reaming element mounting portion 38.

Figure 20:
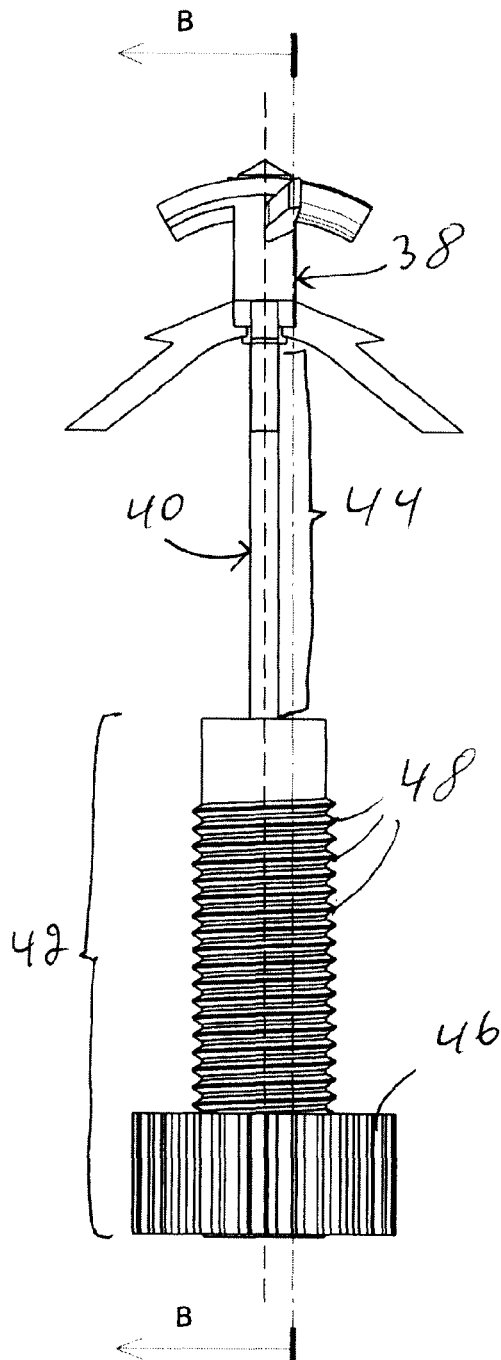
FIG. 20, in a side elevation view, illustrates an actuator, the actuator being part of the acetabular reamer shown in FIGS. 1 to 7.
Figure 21:
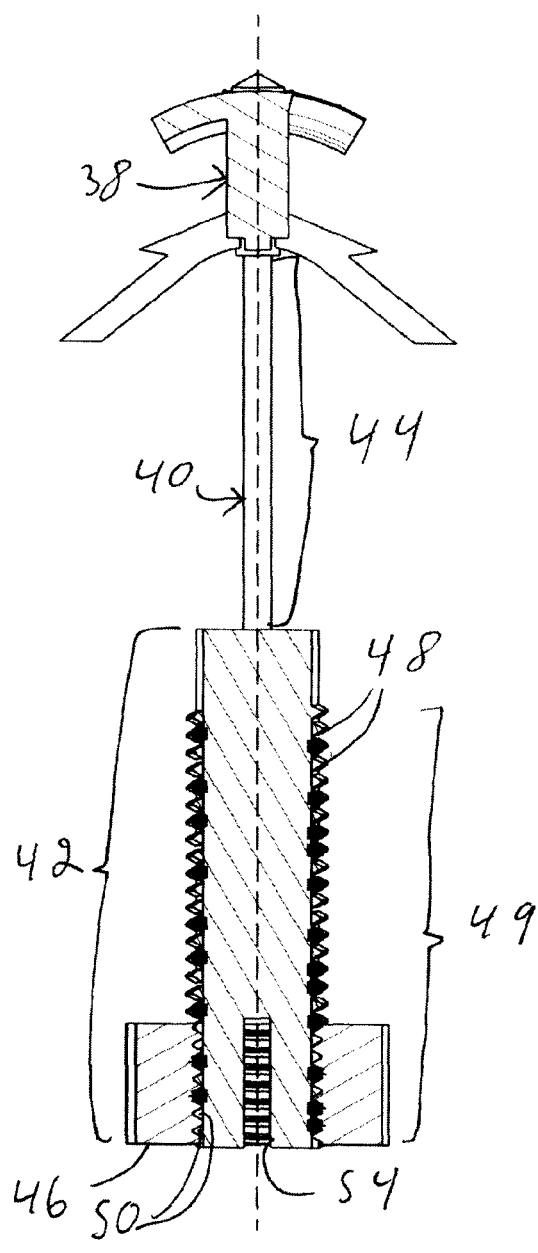
FIG. 21, in a cross-sectional view taken along the line B-B shown in FIG. 20, illustrates the actuator shown in FIG. 21.

Referring to FIGS. 20 and 21, the mounting portion support 40 defines a support proximal end section 42 and a substantially longitudinally opposed support distal end section 44. For example, the mounting portion support 40 takes the form of a substantially elongated component including a substantially cylindrical support distal end section 44 and a substantially cylindrical support proximal end section 42 extending therefrom. The support distal end section 44 typically has smaller diameter than the support proximal end section 42.

In some embodiments of the invention, the actuator 16 further includes a nut 46 mounted to the body 16 so as to extend into the access aperture 34 (not shown in FIGS. 20 and 21). As seen in FIG. 21, support threads 48 present in a threaded section 49 engage nut threads 50 of the nut 46 and are formed into the mounting portion support 40. For example the mounting portion support 40 defines the threaded section 49 that extends substantially longitudinally therealong into the support proximal end section 42. The nut 46 is threaded onto the threaded section 49 so as to be rotatable thereabout.

The nut 46 is operatively coupled to the body 12 so as to be substantially longitudinally substantially fixed relatively to the body 12. For example, this is achieved by providing a nut 46 that extends radially over a distance such that the nut 46 is prevented from entering into the body recess 26 outside of the region defines by the access aperture 34. Rotating the nut 46 relatively to the body 12 therefore moves the mounting portion support 40 substantially longitudinally along the body 12.

A rotation stopper 54 is provided for preventing the mounting portion support 40 from rotating relatively to the body recess 26. For example, the rotation stopper 54 takes the form of a slit extending longitudinally into the support proximal end section 42 and positioned, configured and dimensioned to engage the recess protrusion 32 so as to be fixed in rotation about the rotation axis 13 relatively thereto.

Figure 6:
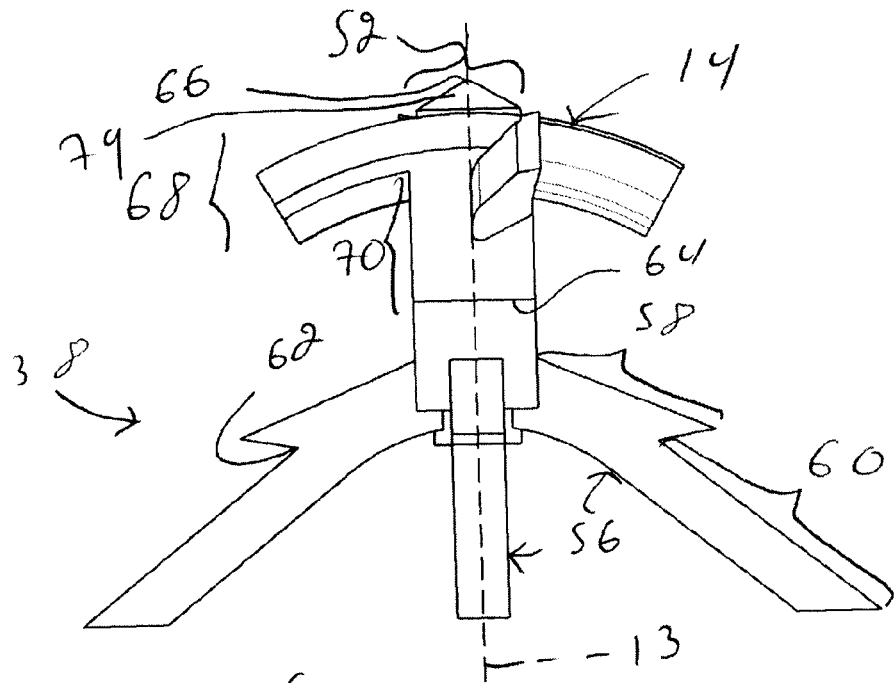
FIG. 6, in a side elevation view, illustrates a portion of an actuator of the acetabular reamer shown in FIGS. 1 to 5b, the portion of the actuator being shown coupled to a reaming element of a first type.
Figure 7:
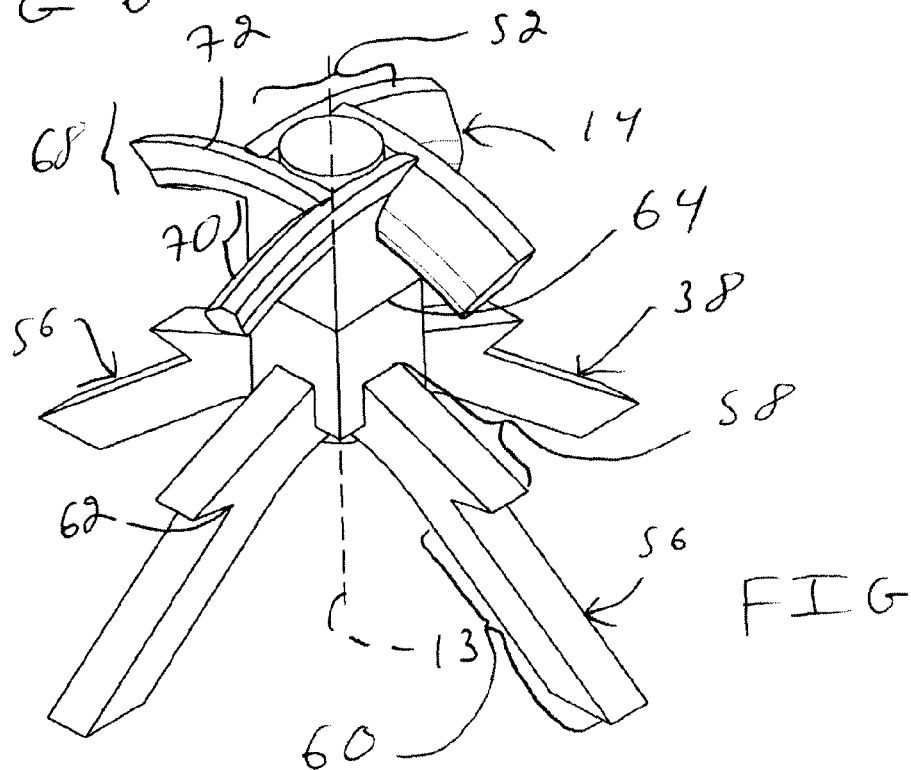
FIG. 7, in a perspective view, illustrates the portion of the actuator shown in FIG. 6 coupled to the reaming element of the first type.
Figure 13:
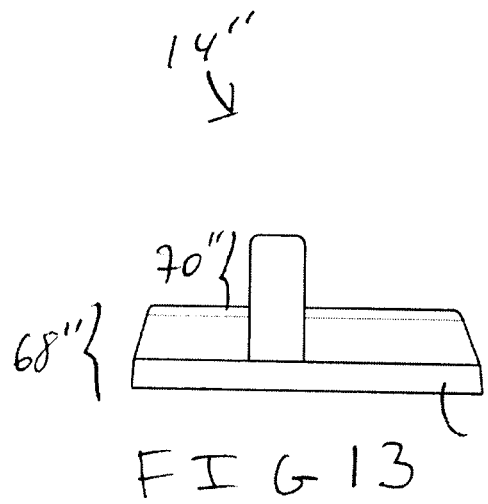
FIG. 13, in a top plan view, illustrates the reaming element of the third type shown in FIG. 12.
Figure 12:
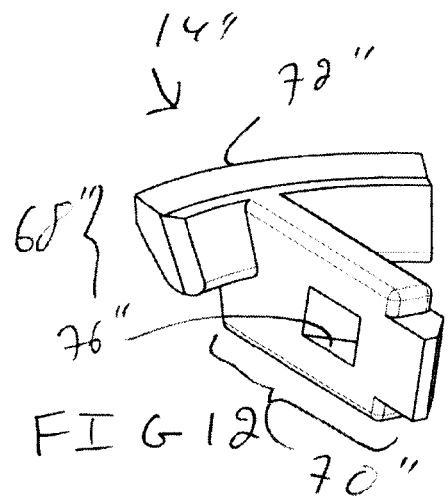
FIG. 12, in a perspective view, illustrates a reaming element of a third type included in the acetabular reamer shown in FIGS. 1 to 7.
Figure 14:
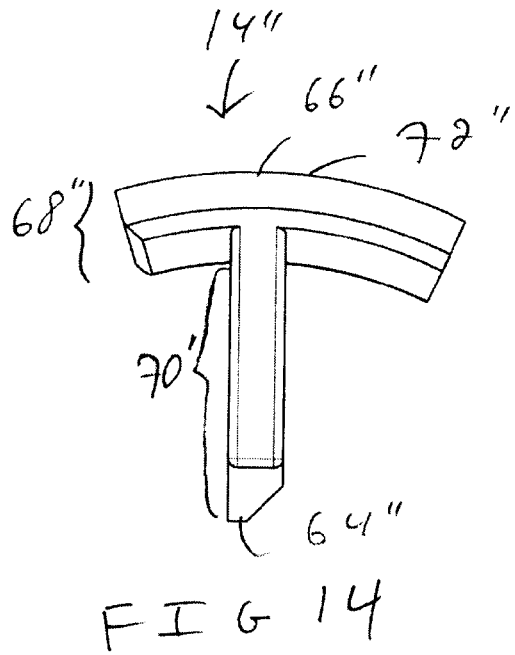
FIG. 14, in a side elevation view, illustrates the reaming element of the third type shown in FIGS. 12 and 13.
Figure 15:
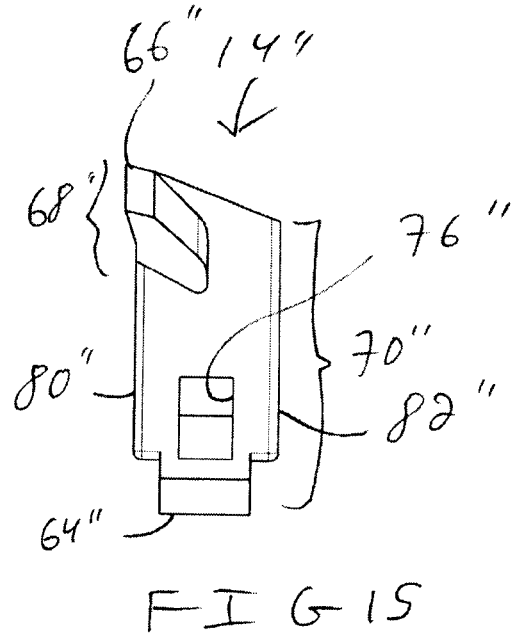
FIG. 15, in a front elevation view, illustrates the reaming element of the third type shown in FIGS. 12 to 14.

Referring to FIGS. 6 and 7, the reaming element mounting portion 38 includes a radially central portion 52 from which arms 56 extend substantially outwardly. Each of the arms 56 includes an arm first section 58 and an arm second section 60 extending therefrom. The arm first section 58 extends from the radially central portion 52. The radially central portion 52, the arm first sections 58 and the arm second sections 60 are provided for mounting thereto respectively a reaming element of the first type 14, reaming elements of the second type 14' and reaming elements of the third type 14".

The arms 56 and the reaming elements 14, 14' and 14" are configured and sized such that the reaming elements 14, 14' and 14" are moved between the reaming element inner and outer portions when the mounting portion support 40 is moved longitudinally along the body 12. Also, the mounting portion support 40 is substantially longitudinally movable along the body 12 with the arms 56 keeping a substantially constant circumferential orientation relatively to the body 12.

In the specific embodiment of the invention shown in the drawings, the reaming element of the first type 14 extends substantially longitudinally away from the mounting portion support 40 from the radially central portion 52. In some embodiments of the invention, the reaming element of the first type 14 is removably mountable to the mounting portion support 40. In other embodiments of the invention, the reaming element of the first type 14 extends integrally from the mounting portion support 40. The reaming elements of the second type 14' are each mounted to a respective arm first section 58 so as to be slidably movable therealong and the reaming elements of the third type 14" are each mounted to a respective arm second section 60 so as to be slidably movable therealong.

It has been found that including four substantially circumferentially equally spaced apart arms 56 provides an acetabular reamer 10 producing relatively small amounts of vibration when used to ream the acetabulum. However, it is within the scope of the invention to include any suitable number of arms 56 in the acetabular reamer 10. Yet, furthermore, while the acetabular reamer 10 shown in the drawings includes three types of reaming elements 14, 14' and 14" and includes arms 56 to which two reaming elements 14' and 14" are mountable, it is within the scope of the invention to have acetabular reamers 10 including arms 56 to which any other suitable number of reaming elements 14, 14' and 14" is mountable.

It has been found that having an arm first section 58 extending at an angle of about 113 degrees relatively to the rotation axis 13 and having an arm second section 60 extending at an angle of about 129 degrees relatively to the rotation axis 13 provides an acetabular reamer 10 able to produce relatively spherical surfaces with a relatively large range of motion for the reaming elements 14, 14' and 14". Therefore, the arms first and second sections 58 and 60 are angled relatively to each other. Also, other values of the above-mentioned angles are within the scope of the invention.

In some embodiments of the invention, a recess 62 is formed at the junction between the arms first and second sections 58 and 60. The recess 62 extends towards the radially central portion 52 into the arm first section 58 and increases the range of motion through which the reaming elements of the third type 14" are movable along the arm second sections 60.

As mentioned hereinabove and seen in FIG. 18, the acetabular reamer 10 includes three types of reaming elements 14, 14' and 14". Each type of reaming elements 14, 14' and 14" is mounted at a respective distance from the rotation axis 13. The reaming element of the first type 14 is mounted to the radially central portion 52. Reaming elements of the second type 14' are mounted to the arm first sections 58 and reaming elements of the third type are mounted to the arm second sections 60. The arms 56 are substantially elongated and each define an arm longitudinal direction. The reaming elements of the second and third types 14' and 14" are mounted to the arms 56 so as to be movable substantially longitudinally therealong and being substantially prevented from moving in any direction substantially perpendicular to the arm longitudinal direction, as described in further details hereinbelow.

The reaming element of the first type 14 is better illustrated in FIGS. 6 and 7. As seen in FIG. 6, the reaming element of the first type 14 includes a reaming element proximal end 64 and a reaming element distal end 66 substantially opposed to the reaming element proximal end 64. The reaming element of the first type 14 includes a reaming portion 68 located substantially adjacent the reaming element distal end 66 and a reaming element-to-actuator coupling portion 70 located substantially adjacent the reaming element proximal end 64. The reaming portion 68 is provided for reaming the acetabulum of the patient for which a hip replacement surgery is performed. The reaming element-to-actuator coupling portion 70 couples the reaming element of the first type 14 to the actuator 16.

The reaming portion 68 defines a reaming surface 72, better shown, for example, in FIG. 7. In a specific embodiment of the invention, the reaming surface 72 is a cutting surface having a substantially smooth and substantially arcuate configuration. In the embodiment of the invention shown in the drawings, the reaming surface 72 includes four substantially arcuate reaming surface sections 74 each located eccentrically relatively to the rotation axis 13 and angled in a plane substantially perpendicular to the rotation axis 13 so as to be substantially perpendicular to each other.

In some embodiments of the invention, the reaming element of the first type 14 includes a point 79 (seen in FIG. 6 only), taking the form, for example, of a substantially conical element extending substantially longitudinally towards the reaming element distal end 66. The point 79 is usable for stabilizing the acetabular reamer 10 about the rotation axis 13 when the acetabular reamer 10 is used.

Referring to FIGS. 8 to 11, there is shown in greater details the reaming element of the second type 14'. As seen in FIG. 11, the reaming element of the second type 14' defines a reaming element proximal end 64' and an opposed reaming element distal end 66'. The reaming element of the second type 14' includes a reaming portion 68' for reaming the acetabulum of the patient and a reaming element-to-actuator coupling portion 70' mechanically coupled to the reaming portion 68'. For example, the reaming element-to-actuator coupling portion 70' extends integrally from the reaming portion 68'.

The reaming element-to-actuator coupling portion 70' is mountable to the actuator 16 and, more specifically, to the arm first section 58, such that the reaming element of the second type 14' is substantially longitudinally movable therealong while substantially prevented from moving in any direction perpendicular to the arm first section 58 relatively thereto. Therefore, the reaming element of the second type 14' is both actively deployable and retractable by the actuator 16.

For example, this is achieved through the use of a mounting aperture 76', better seen in FIGS. 8 and 11, extending through the reaming element-to-actuator coupling portion 70', the arm first section 58 extending through the mounting aperture 76' when the reaming element of the second type 14' is mounted to the arm first section 58'.

As shown for example in FIG. 9, the reaming portion 68' defines a radially outwardmost reaming surface 72' taking the form, for example, of a cutting surface having a substantially smooth arcuate configuration. The reaming surface 72' is the portion of the reaming element of the second type 14' that reams the acetabulum when the acetabular reamer 10 is in use.

As better seen in FIG. 11, the reaming element 14' defines substantially opposed abutment surfaces 80' and 82' located substantially opposed to each other and extending between the reaming element proximal and distal ends 64' and 66". The mounting aperture 76' is located between the abutment surfaces 80' and 82'. The abutment surfaces 80' and 82' are provided for engaging the reaming element lock 18 when the reaming element lock 18 is in the locked configuration.

The reaming element of the second type 14' has a configuration such that mechanical interferences with adjacent reaming elements 14, 14' and 14" are minimized so as to allow for a maximal range of motion along the arm first section 58' of the reaming element of the second type 14'. The exact configuration of the reaming element of the second type 14' depends on the configuration of adjacent reaming elements 14, 14' and 14" and includes, for example, recesses 84' and 86' located substantially adjacent the reaming element proximal end 64', the recesses 84' and 86' being dimensioned to receive thereinto portions of adjacent reaming elements 14, 14', 14" at predetermined positions of the reaming elements 14, 14', 14" between the reaming element inner and outer positions.

In addition, as better seen in FIG. 8, the reaming element of the second type 14' defines bevelled surfaces 88' and 90' located respectively adjacent the reaming element proximal and distal ends 64' and 66'. The bevelled surfaces 88' and 90' are configured to provide a space through which adjacent reaming elements 14, 14' and 14" are insertable.

FIGS. 12 to 15 illustrate the reaming element of the third type 14". The reaming element of the third type 14" has a configuration that is substantially similar to the configuration of the reaming element of the second type 14', and is therefore not described in greater details. In FIGS. 12 to 15, reference numerals having a " suffix designate sections, portions and structures of the reaming element of the third type 14" having a function similar to the function of sections, portions and structures of the reaming element of the second type 14' having the same numerical designation to which a ' suffix has been added. More specifically, the reaming element 14" defines reaming element proximal and distal ends 64" and 66", reaming portion 68", reaming element-to-actuator coupling portion 70', reaming surface 72" and mounting aperture 76".

Figure 16:
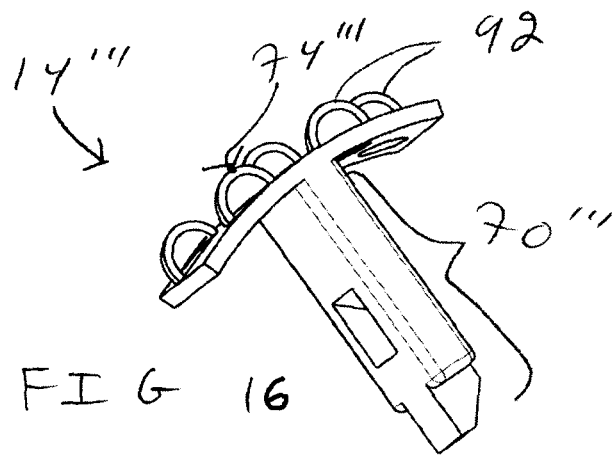
FIG. 16, in a perspective view, illustrates a reaming element in accordance with an alternative embodiment of the present invention.

As shown in FIG. 16, in some embodiments of the invention, the reaming surfaces 72, 72' and 72" are not cutting surfaces but instead a grating surfaces. Therefore, in these embodiments, the reaming elements 14, 14', 14", for example the alternative reaming element of the second type 14'" shown in FIG. 16, include an alternative reaming surface 74" defining asperities 92 extending therefrom substantially away from the reaming element-to-actuator coupling portion 70'.

Figure 17:
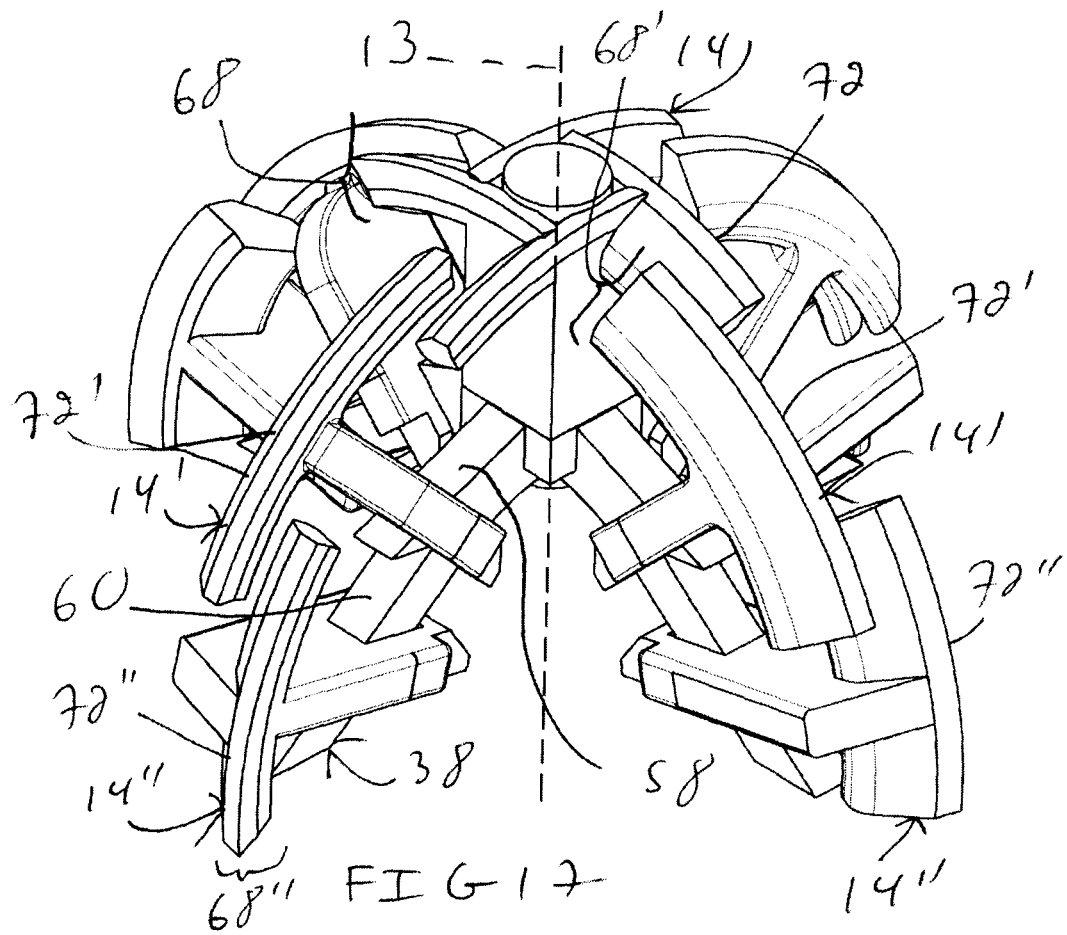
FIG. 17, in a perspective view, illustrates a coupling between the reaming elements shown in FIGS. 8 to 15 and the actuator shown in FIGS. 6 and 7.

FIG. 17 illustrates the manner in which the reaming elements 14, 14', 14" are mounted to the reaming element mounting portion 38. As seen in this Figure, the reaming surfaces 72, 72' and 72" of the reaming elements of the first second and third types 14, 14' and 14" are distributed along at least one meridian of a substantially spherical-cap-shaped surface rotatable about the rotation axis 13 with their reaming surfaces 72, 72' and 72" having a substantially smooth and substantially arcuate configuration oriented along the at least one meridian. In some embodiments of the invention, the reaming portions 68, 68' and 68" are each substantially arc-segment shaped and extend over a length such that reaming portions 68, 68' and 68" of reaming elements 14, 14' and 14" located on a common meridian substantially overlap. To that effect, adjacent reaming portions 68, 68' and 68" located on a common meridian are substantially circumferentially slightly offset from each other.

The reaming portions 68, 68' and 68" are shaped and dimensioned such that the global reaming surface formed thereby is formed on a substantially spherical cap (not shown in the drawings). It has been found that having an acetabular reamer 10 having a dimension and a configuration such that this spherical cap (not shown in the drawings) has a radius of curvature varying from about 44 mm to about 66 mm provides an acetabular reamer 10 suitable for use in most hip replacement surgeries. Advantageously, the proposed acetabular reamer then has a ratio of about 1.5 between the radius of the smallest reamable cavity and the largest reamable cavity, which is relatively large when compared to existing acetabular reamers.

In some embodiments of the invention, the reaming portions 68, 68' and 68" of reaming elements 14, 14' and 14" located on a same meridian substantially overlap over the entire range of motion of the reaming elements 14, 14' and 14". However, in alternative embodiments of the invention, there is no such overlap and, in yet other embodiments of the invention, the reaming elements 14, 14' and 14", overlap only over a portion of the range of motion of the reaming elements 14, 14' and 14". This overlap allows for the production of a relatively smooth surface when reaming the acetabulum of a patient without requiring that the acetabular reamer 10 be moved in a substantially ball-joint-like motion inside the patient.

Figure 19:
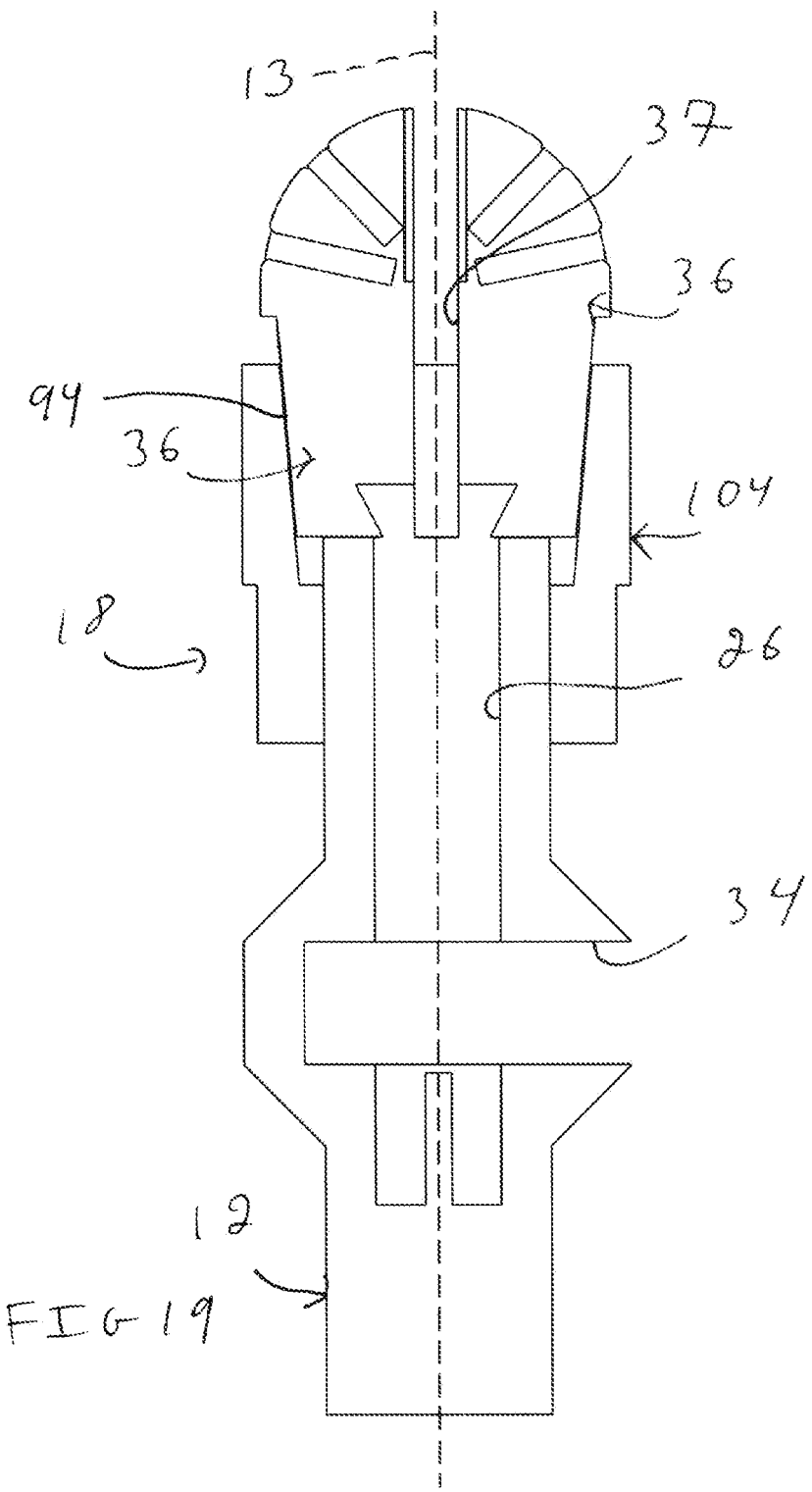
FIG. 19, in a side cross-sectional view with parts removed, illustrates the acetabular reamer shown in FIGS. 1 to 7.

As seen in FIGS. 19, 22*a* and 22*b*, the reaming element lock 18 includes substantially circumferentially spaced apart locking components 36 mounted to the body 12 so as to be movable between a locked position, shown in FIG. 22*a*, and an unlocked position, shown in FIG. 22*b*. The reaming element lock 18 includes at least two locking components 36. In the embodiment of the invention shown in the drawings, the reaming element lock 18 includes four locking components 36. The locking components 36 define substantially circumferentially extending gaps 37 therebetween. As detailed hereinbelow, the reaming elements of the second and third types 14' and 14" are partially inserted in the gap 37. The reaming element lock 18 also includes a lock actuating element 104 operatively coupled to the locking components 36 for configuring the reaming element lock 18 between the locked and unlocked configurations.

In the unlocked position, the reaming element lock 18 is in the unlocked configuration, and the locking components 36 are spaced apart by a larger distance than in the locked position. When the locking components 36 are in the locked position, the reaming element lock 18 is in the locked configuration. The locking components 36 frictionally engage the reaming elements of the second and third types 14' and 14" when the locking components 36 are in the locked position.

Figure 18:
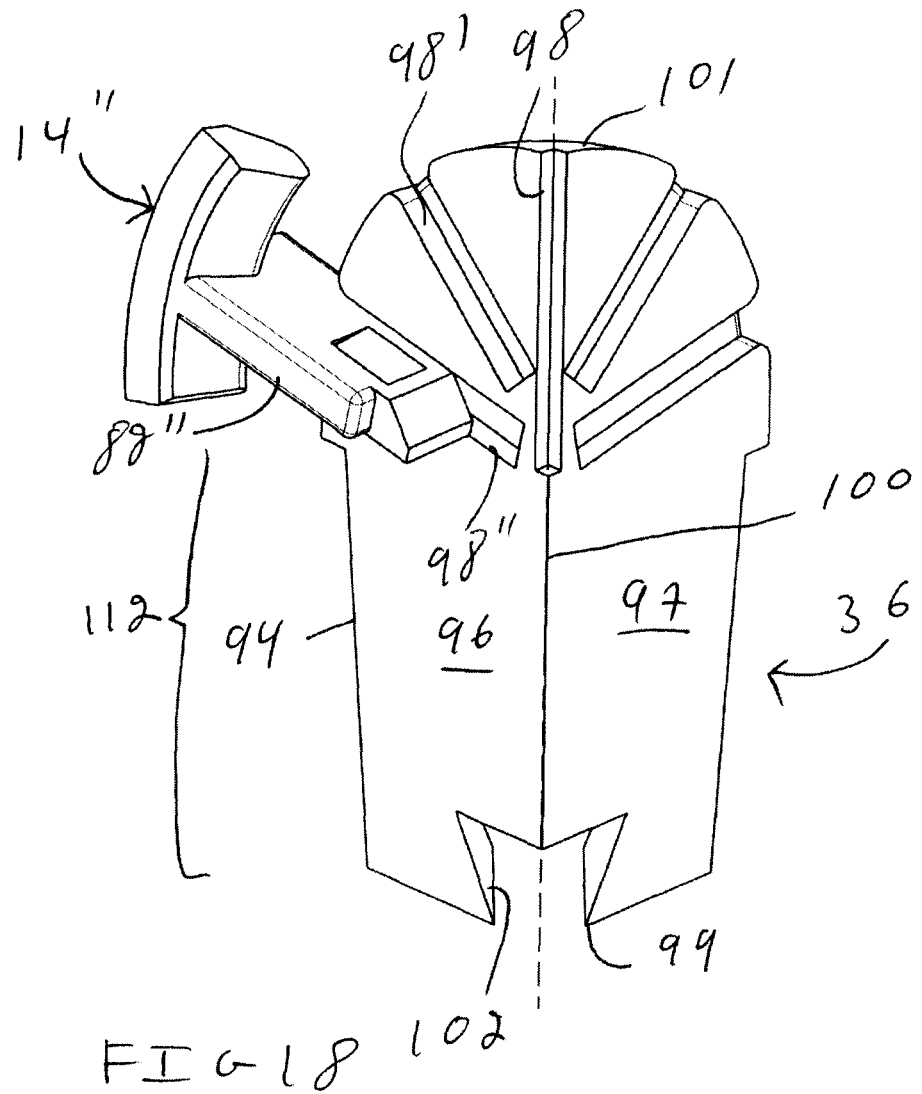
FIG. 18, in a perspective view, illustrates a coupling between a reaming element and a locking component included in the acetabular reamer shown in FIGS. 1 to 7.

FIG. 18 illustrates one of the locking components 36 to which a reaming element of the second type 14" is mounted. The locking component 36 defines a locking component distal end 101 and an opposed locking component proximal end 99. The locking component 36 also defines a locking component radially outwardmost surface 94 and two locking component lateral surfaces 96 and 97 extending therefrom, the two locking components lateral surfaces 96 and 97 sharing a common edge 100 and being angled at an angle of about 90 degrees relatively to each other. When the locking component 36 is mounted to the body 12, the locking component radially outwardmost surface 94 faces outwardly. The locking component 36 includes a locking component actuating portion 112 for coupling the locking component 36 to the lock actuating element 104 (not shown in FIG. 18).

The locking component radially outwardmost surface 94 has a substantially arcuate configuration and the locking component lateral surfaces 96 and 97 have a substantially planar configuration. Therefore, the four locking components 36, when put adjacent to each other so that their respective locking component lateral surfaces 96 and 97 extend substantially parallel to each other form a structure having a rotational symmetry with the locking component radially outwardmost surfaces 94 facing substantially radially outwardly.

In some embodiments of the invention, the locking component actuating portion 112 includes a portion of the locking component 36 extending from the locking component proximal end 99 towards the locking component distal end 101. The locking component actuating portion 112 includes a portion of locking component radially outwardmost surface 94 shaped similarly to an arc segment of a substantially frustroconical surface and tapers in a direction leading towards the locking component proximal end 99.

Grooves 98, 98' and 98" are formed into the locking component 36 for slidably receiving respectively a portion of the reaming elements of the first, second and third types 14, 14' and 14" thereinto for mounting the reaming elements 14, 14' and 14" thereto and guiding the reaming elements 14, 14' and 14" therealong when the reaming elements 14, 14' and 14" are moved between said reaming element inner and outer positions. The groove 98 extends substantially longitudinally and is provided for receiving a portion of the reaming element of the first type 14. The grooves 98' extend at an angle of about 44 degrees relatively to the rotation axis 13 and have a substantially U-shaped configuration for receiving thereinto a portion of the reaming element of the second type 14'. More specifically, the grooves 98' are provided for each frictionally engaging one of the abutment surfaces 82' and 80' of the reaming elements of the second type 14'. The grooves 98" extend at an angle of about 78 degrees relatively to the rotation axis 13 and have a substantially U-shaped configuration for receiving thereinto a portion of one of the reaming elements of the third type 14". More specifically, the grooves 98" are provided for each frictionally engaging one of the abutment surfaces 82" and 80" of the reaming elements of the third type 14".

As seen in FIGS. 22*a* and 22*b*, and as mentioned hereinabove, the locking components 36 are mountable to the body 12 so as to be movable between a locked position and an unlocked position. In the locked position, the locking components abut against and frictionally engage the abutment surfaces 80', 82', 80" and 82" and the reaming element of the first type 14, and therefore frictionally prevent movement of the reaming elements 14, 14' and 14" relatively to the locking components 36. In the unlocked position, the locking components 36 are spaced apart by a large distance than in the locked position, thereby releasing a grip exerted onto the reaming elements 14, 14' and 14".

Referring to FIG. 18, in some embodiments of the invention, each locking component 36 defines a guiding groove 102 for mounting the locking component 36 to the locking component attachment 35. For example, the guiding groove 102 bisects and extends from the intersection of the locking component lateral surfaces 96 and 97 towards the locking component radially outwardmost surface 94 substantially midway between the locking component lateral surfaces 96 and 97 and substantially adjacent to the locking component proximal end 99. The guiding groove 102 is tapered both in a direction loading towards the locking component proximal end 99 and in a direction loading towards the locking component radially outwardmost surface 94. The locking component attachments 35 take the form of protrusions having a shape complementary to the guiding grooves 102 and are received within the guiding groove 102.

In some embodiments of the invention, the lock actuating element 104 takes the form of a sleeve mounted to the body 12 so as to be substantially longitudinally movable relatively thereto. The lock actuating element 104 is also operatively coupled to the locking components 36 so as to move the locking components 36 between the locked positions and the unlocked positions. As seen in FIG. 3, the lock actuating element 104 defines a locking component mounting passageway 106 extending substantially longitudinally and a body mounting passageway 108 extending substantially longitudinally therefrom.

The locking component actuating portions 112 of the locking components 36 are at least partially located in the locking component mounting passageway 106, the locking component mounting passageway 106 engaging the locking components 36 in a manner such that the locking components 36 are moved between the locking component locked and unlocked positions when the lock actuating element 104 is moved substantially longitudinally along the body 12.

For example, the locking component mounting passageway 106 is substantially frustro-conical and has a substantially tapered configuration in a direction leading towards the body proximal end section 20. The locking component mounting passageway 106 is substantially parallel to the actuating portion radially outwardmost surfaces 94. The body mounting passageway 108 has a substantially cylindrical configuration for mounting to a portion of the body 12 having a substantially cylindrical configuration having a similar diameter.

In some embodiments of the invention, the lock actuating element 104 is slidably mounted to the body 12. However, in alternative embodiments of the invention, the lock actuating element 104 is mountable to the body 12 in any other suitable manner allowing the lock actuating element 104 to move substantially longitudinally relatively to the body 12. For example, lock actuating element 104 may be screwable onto the body 12 through the use of threads formed both into the lock actuating element 104 and into the body 12 (this variant not being illustrated).

The lock actuating element 104 is movable between a proximal position and a distal position. In the proximal position (seen for example in FIG. 22b), the locking component mounting passageway 106 is positioned such that the locking components 36 are spaced apart by a larger distance than in the distal position. In the distal position (seen for example in FIG. 22a), the locking component mounting passageway 106 biases the locking components 36 towards each other.

In use, the intended user (not shown in the drawings) positions the lock actuating element 104 in the proximal position and the locking components 36 in the unlocked positions. This reduces the friction exerted by the locking components 36 onto the reaming elements 14, 14' and 14", and allows the intended user (not shown in the drawings) to use the actuator 16 to position the reaming elements 14, 14' and 14" in their reaming element inner positions. Subsequently, the locking components 36 are moved to their locked positions by moving the lock actuating element 104 to the distal position, and the acetabular reamer 10 is inserted in the body of the patient. Reaming is then performed. When there is a need to expand the dimension of the acetabular reamer 10, the intended user (not shown in the drawings) leaves the acetabular reamer inside the patient and adjusts the position of the reaming elements 14, 14', 14" as described hereinabove such that the reaming elements 14, 14', 14" are moved over a desired distance towards their reaming element outer positions.

In the embodiment of the invention shown in the drawings, this is achieved by rotating the nut 46, thereby translating the actuator 16 relatively to the body 12, which consequently moves the reaming elements 14, 14' and 14" relatively to the locking components 36 and relatively to the body 12. This is achieved because the arm first and second sections 58 and 60 are substantially rectilinear and angled relatively to the rotation axis 13. For example, the thread count on the nut 46 and body 12 is such that a predetermined fraction of a whole turn of the nut 46 results in a convenient predetermined expansion the reaming elements 14, 14', 14". For example, each turn of the nut 46 corresponds to a movement of about 1 mm of the reaming elements 14, 14' and 14" respectively relatively to the grooves 98, 98' and 98".

Once a suitable position for the reaming elements 14, 14' and 14" has been achieved, the locking component 36 is configured into the locked configuration by moving the lock actuating element 104 away from the body proximal end section 20, which guides the locking components 36 towards each other. In this configuration, the reaming elements 14, 14' and 14" are supported by the locking components 36 and, therefore, only relatively small forces are transmitted to the actuator 16 by the reaming elements 14, 14' and 14".

In alternative embodiments of the invention, the actuator 16 takes any other suitable form. For example, the actuator 16 is configured so as to be operable further away from the reaming elements 14, 14' and 14" than in the acetabular reamer 10. Also, in some embodiments of the invention, a handle (not shown in the drawings) is provided for allowing a surgeon to handle the acetabular reamer 10 relatively easily and precisely.

Figure 23:
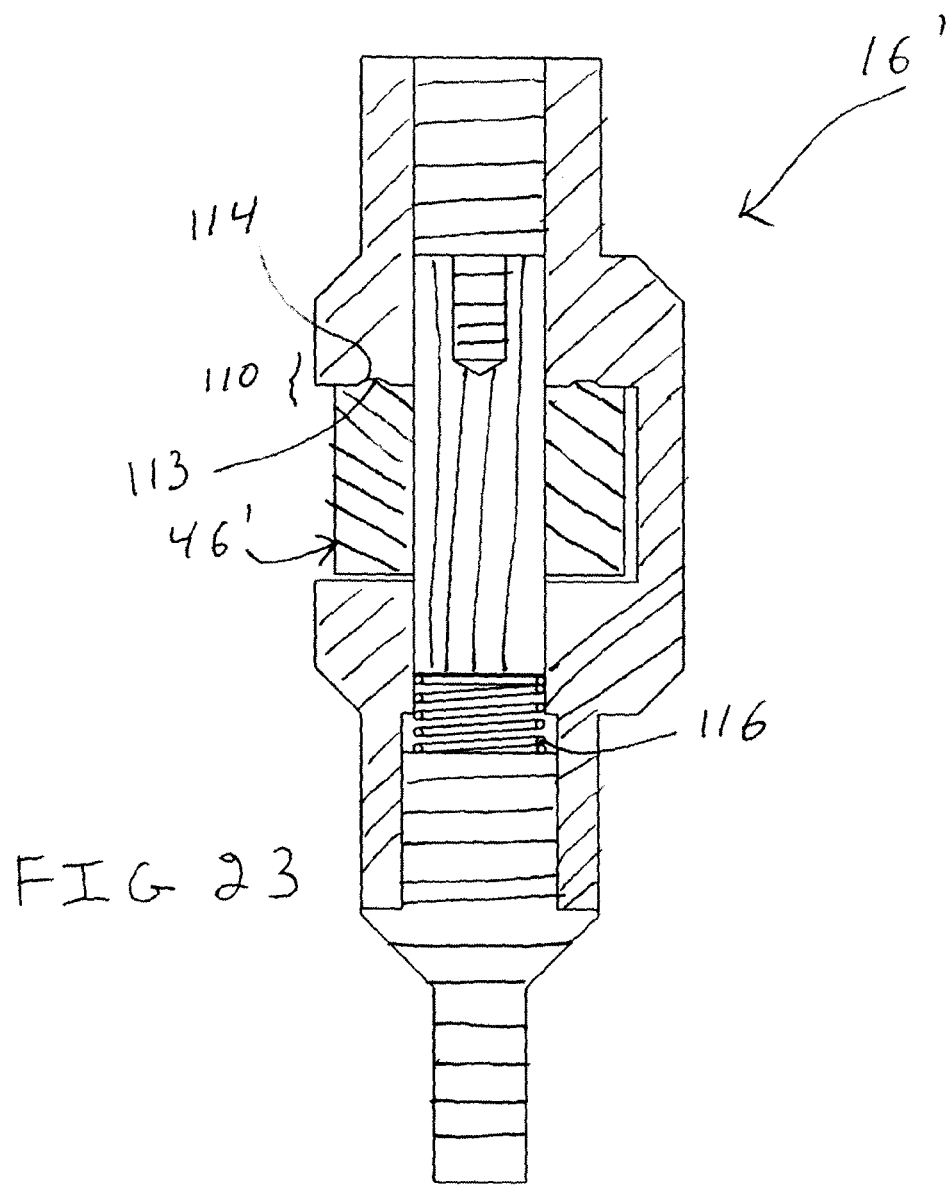
FIG. 23, in a partial side cross-sectional view, illustrates an actuator for the acetabular reamer of FIGS. 1 to 7 in accordance with an alternative embodiment of the invention.
Figure 24:
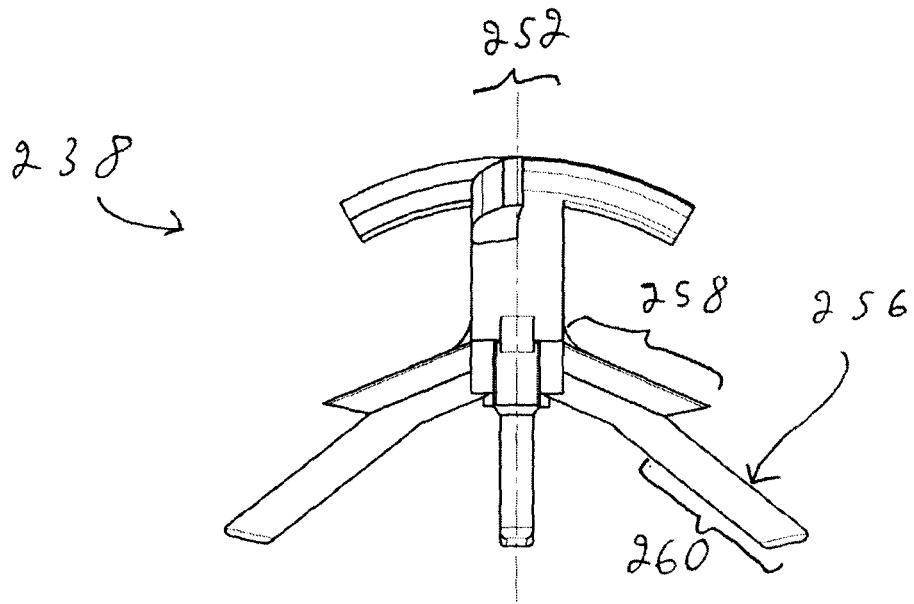
FIG. 24, in a partial side elevation view, illustrates an actuator in accordance with another alternative embodiment of the invention.
Figure 25:
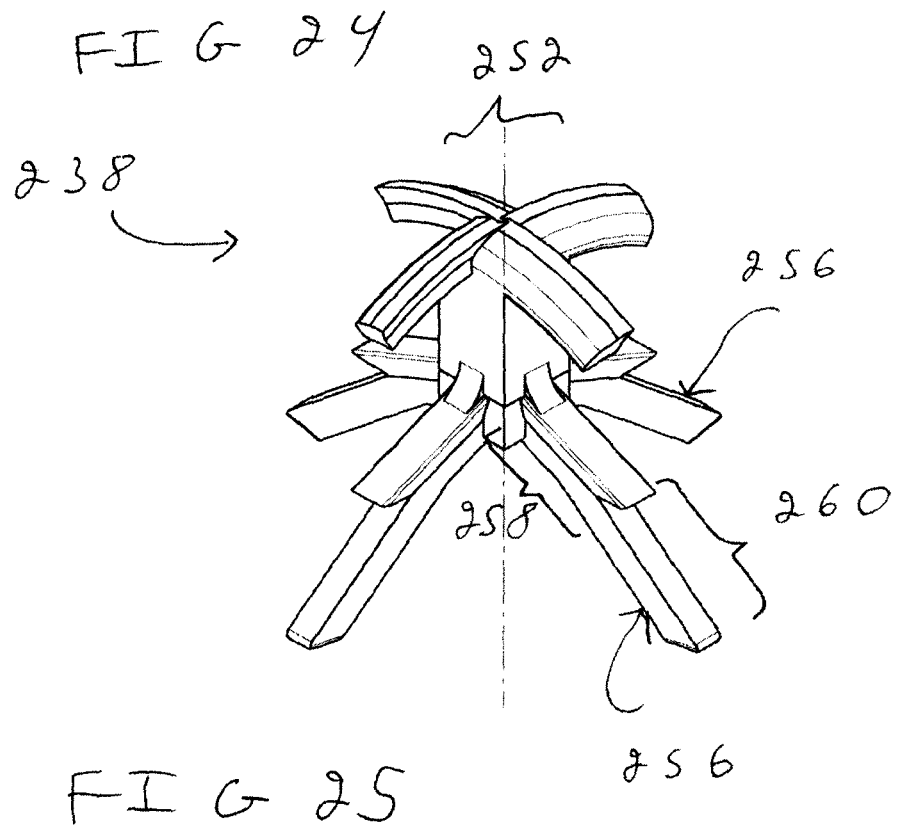
FIG. 25, in perspective view, illustrates the actuator shown in FIG. 24.
Figure 27:
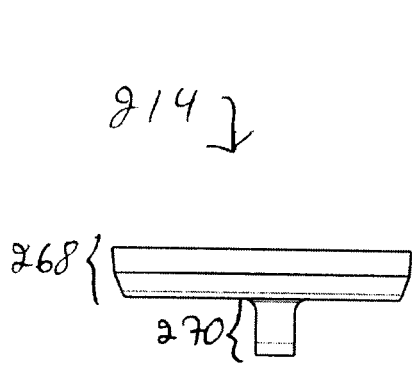
FIG. 27, in a top plan view, illustrates the reaming element of the second type shown in FIG. 26.

In an alternative embodiment of the invention shown in FIG. 23, an alternative actuator 16' defines a deployment indicator 110 for moving the actuator 16' in discrete steps so as to move the reaming elements 14, 14' and 14" in (all not shown in FIG. 23) discrete steps relatively to the rotation axis 13 (not shown in FIG. 23). For example, the deployment indicator 110 includes a tactile deployment indicator. An example of such a tactile deployment indicator 110 takes the form of a nut 46' including substantially longitudinally extending protrusions 113. The nut 46' is mounted in an access aperture 34 allowing relatively small movements of the nut 46' longitudinally therealong. The body 12 defines longitudinally extending recesses 114 for receiving the protrusions 113. The nut 46' is biased towards the recesses 114 by a biasing element 116, for example taking the form of a coil spring. Therefore, as the nut 46' is rotated, when predetermined angular positions of the nut 46' are reached, the protrusions 113 engage the recesses 114, which transmits a small impact force to the intended user through the nut 46 and indicates that the predetermined angular position has been reached. To continue rotating the nut 46', the intended user exerts a force large enough on the nut 46' so that the protrusions 113 are pushed out of the recesses 114.

FIGS. 24 to 29 illustrate an alternative reaming element mounting portion 238 and an alternative reaming element of the second type 214. The reaming element mounting portion 238 is similar to the reaming element mounting portion 38 described hereinabove and includes a radially central portion 252 from which arms 256 extend substantially outwardly. Each of the arms 256 includes an arm first section 258 and an arm second section 260 extending therefrom. The arm first section 258 extends from the radially central portion 252. However, instead of having a substantially rectangular cross-section, the arm first section 258 has a substantially trapezoidal transversal cross-sectional configuration. The arm first section 258 is provided for mounting the alternative reaming element of the second type 214.

Referring to FIGS. 26 to 29, there is shown in greater details the alternative reaming element of the second type 214. As seen for example in FIG. 28, the reaming element of the second type 214 defines a reaming element proximal end 264 and an opposed reaming element distal end 266. The reaming element of the second type 214 includes a reaming portion 268 for reaming the acetabulum of the patient and a reaming element-to-actuator coupling portion 270 mechanically coupled to the reaming portion 268. For example, the reaming element-to-actuator coupling portion 270 extends integrally from the reaming portion 268.

The reaming element-to-actuator coupling portion 270 is mountable to the to the arm first section 258 such that the reaming element of the second type 214 is substantially longitudinally movable therealong while substantially prevented from moving in any direction perpendicular to the arm first section 258 relatively thereto. Therefore, the reaming element of the second type 214 is both actively deployable and retractable by the arm first section 258.

Figure 26:
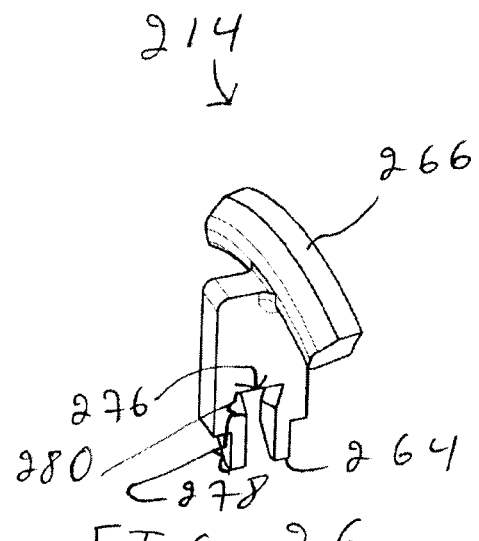
FIG. 26, in a perspective view, illustrates an alternative reaming element of the second type usable with the actuator shown in FIGS. 24 and 25.
Figure 28:
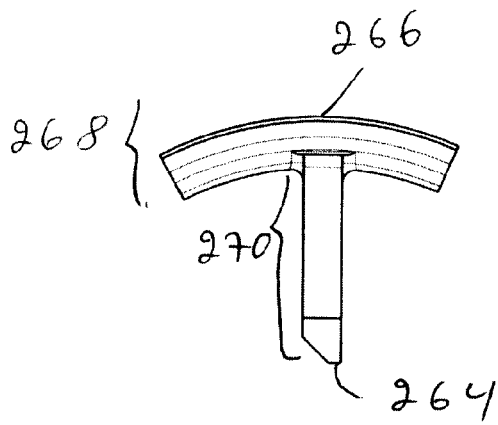
FIG. 28, in a side elevation view, illustrates the reaming element of the second type shown in FIGS. 25 and 27.
Figure 29:
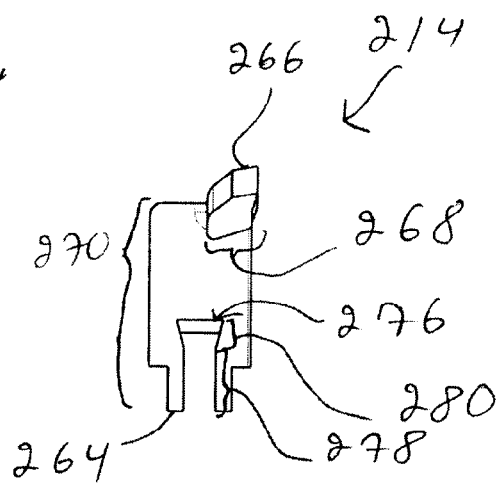
FIG. 29, in a front elevation view, illustrates the reaming element of the second type shown in FIGS. 26 to 28.

For example, this is achieved through the use of a mounting groove 276, better seen in FIGS. 26 and 29, extending into the reaming element-to-actuator coupling portion 270 from reaming element proximal end 264. The mounting groove 276 includes a groove proximal section 278 and a groove distal section 280. The groove distal section 280 is spaced apart from the reaming element distal end 266 and has a substantially trapezoidal lateral cross-sectional configuration tapering towards the reaming element distal end 266 that is substantially similar to the lateral cross-sectional configuration of the arm first section 258. The groove distal section 280 is mountable to the arm first section 258 so as to be substantially longitudinally movable therealong. The groove proximal section 278 extends between the reaming element proximal end 264 and the groove distal section 280 and is configured for allowing free movement of the arm second section 260 therethrough. For example, the groove proximal section 278 has a substantially rectangular cross-sectional configuration. The mounting groove 276 is advantageous in some embodiments of the invention as the open nature of the proximal extremity of the mounting groove 276 allow for manufacturing a relatively compact acetabular reamer 10.

The reaming portion 268 is substantially similar to the reaming portion 68' and, with the exception of the mounting groove 276 replacing the mounting aperture 76', the reaming element-to-actuator coupling portion 270 is substantially similar to the reaming element-to-actuator coupling portion 70'. These elements will therefore not be described in further details herein.

Although the present invention has been described hereinabove by way of preferred embodiments thereof, it can be modified, without departing from the spirit and nature of the subject invention as defined in the appended claims.

What is claimed is:

1. An acetabular reamer for reaming an acetabulum, reaction forces being exerted onto said acetabular reamer by said acetabulum when said acetabulum is reamed, said acetabular reamer comprising:
   a body, said body defining a rotation axis about which said acetabular reamer is rotatable;
   a reaming element operatively coupled to said body so as to be movable between a reaming element inner position and a reaming element outer position relatively thereto, said reaming element being positioned further away from said rotation axis in said reaming element outer position than in said reaming element inner position;
   an actuator operatively coupled to said reaming elements for moving said reaming elements between said reaming element inner and outer positions; and
   a reaming element lock configurable between a locked configuration and an unlocked configuration, said reaming element lock being operatively coupled to said reaming element in a manner such that when said reaming element lock is in said unlocked configuration, said reaming element is freely movable by said actuator between said reaming element inner and outer positions, and when said reaming element lock is in said locked configuration, said reaming element lock prevents said reaming element from moving relatively to said body;
   said reaming element lock being configured, sized and operatively coupled to said reaming element and said body in a manner such that when said reaming element lock is in said locked configuration and said reaction forces are exerted onto said reaming element, a larger portion of said reaction forces is transmitted to said body than to said actuator;
   said actuator including a reaming element mounting portion for mounting said reaming element thereto, said reaming element mounting portion including a radially central portion and an arm extending outwardly from said radially central portion, said reaming element being mounted to said arm, said actuator also including a mounting portion support for supporting said reaming element mounting portion, said reaming element support being mounted to said body so as to be longitudinally movable therealong;
   said arm and said reaming element being configured and sized such that said reaming element is moved between said reaming element inner and outer portions when said mounting portion support is moved longitudinally along said body, said mounting portion support being longitudinally movable along said body with said arm keeping a constant circumferential orientation relatively to said body, said mounting portion support defining a threaded section extending longitudinally therealong, said actuator including a nut threaded onto said threaded section so as to be rotatable thereabout, said nut being operatively coupled to said body so as to be longitudinally fixed relatively to said body, whereby rotating said nut relatively to said body moves said mounting portion support longitudinally along said body.

2. An acetabular reamer as defined in claim 1, wherein said actuator defines a deployment indicator for moving said actuator in discrete steps so as to move said reaming elements in discrete steps relatively to said rotation axis.

3. An acetabular reamer as defined in claim 2, wherein said deployment indicator includes a tactile deployment indicator.

4. An acetabular reamer for reaming an acetabulum, reaction forces being exerted onto said acetabular reamer by said acetabulum when said acetabulum is reamed, said acetabular reamer comprising:
   a body, said body defining a rotation axis about which said acetabular reamer is rotatable;
   two reaming elements operatively coupled to said body so as to be each movable between a reaming element inner position and a reaming element outer position relatively thereto, said reaming elements being positioned further away from said rotation axis in said reaming element outer position than in said reaming element inner position;
   an actuator operatively coupled to said reaming element for moving said reaming elements between said reaming element inner and outer positions; and
   a reaming element lock configurable between a locked configuration and an unlocked configuration, said reaming element lock being operatively coupled to said reaming elements in a manner such that when said reaming element lock is in said unlocked configuration, said reaming elements are freely movable by said actuator between said reaming element inner and outer positions, and when said reaming element lock is in said locked configuration, said reaming element lock prevents said reaming elements from moving relatively to said body;
   said reaming element lock being configured, sized and operatively coupled to said reaming elements and said body in a manner such that when said reaming element lock is in said locked configuration and said reaction forces are exerted onto said reaming elements, a larger portion of said reaction forces is transmitted to said body than to said actuator;
   wherein
   said actuator includes a reaming element mounting portion for mounting said reaming element thereto, said reaming element mounting portion including a radially central portion and an arm extending outwardly from said radially central portion, said reaming elements being mounted to said arm; and said arm defines an arm first section and an arm second section extending therefrom and angled relatively thereto, said arm first section extending from said radially central portion, each of said two reaming elements being mounted to a respective one of said arm first and second sections.

5. An acetabular reamer as defined in claim 4, wherein said reaming element is removably mounted to said arm.

6. An acetabular reamer as defined in claim 4, wherein said arm is elongated and defines an arm longitudinal direction, said reaming elements being mounted to said arm so as to be movable longitudinally therealong and being prevented from moving in any direction perpendicular to said arm longitudinal direction.

7. An acetabular reamer as defined in claim 4, wherein said actuator includes four circumferentially equally spaced apart arms each extending outwardly from said radially central portion.

8. An acetabular reamer as defined in claim 4, comprising a plurality of reaming elements, said plurality of reaming elements including said two reaming elements, each of said reaming elements from said plurality of reaming elements being operatively coupled to said body so as to be movable between a respective reaming element inner position and a respective reaming element outer position relatively thereto, each of said reaming elements from said plurality of reaming elements being positioned further away from said rotation axis in said respective reaming element outer position than in said respective reaming element inner position.

9. An acetabular reamer as defined in claim 8, wherein each of said reaming elements from said plurality of reaming elements defines a respective reaming portion for reaming said acetabulum, each of said reaming portions defining a respective radially outwardmost reaming surface, said reaming surfaces of said plurality of reaming elements being distributed along at least one meridian of a spherical-cap-shaped surface rotatable about said rotation axis.

10. An acetabular reamer as defined in claim 9, wherein said reaming surfaces distributed along said at least one meridian circumferentially overlap each other along said at least one meridian.

11. An acetabular reamer as defined in claim 10 wherein said reaming surfaces each include a cutting surface having a smooth and arcuate configuration oriented along said at least one meridian.

12. An acetabular reamer for reaming an acetabulum, reaction forces being exerted onto said acetabular reamer by said acetabulum when said acetabulum is reamed, said acetabular reamer comprising:
a body, said body defining a rotation axis about which said acetabular reamer is rotatable;
a reaming element operatively coupled to said body so as to be movable between a reaming element inner position and a reaming element outer position relatively thereto, said reaming element being positioned further away from said rotation axis in said reaming element outer position than in said reaming element inner position;
an actuator operatively coupled to said reaming element for moving said reaming element between said reaming element inner and outer positions; and
a reaming element lock configurable between a locked configuration and an unlocked configuration, said reaming element lock being operatively coupled to said reaming element in a manner such that when said reaming element lock is in said unlocked configuration, said reaming element is freely movable by said actuator between said reaming element inner and outer positions, and when said reaming element lock is in said locked configuration, said reaming element lock prevents said reaming element from moving relatively to said body;
said reaming element lock being configured, sized and operatively coupled to said reaming element and said body in a manner such that when said reaming element lock is in said locked configuration and said reaction forces are exerted onto said reaming element, a larger portion of said reaction forces is transmitted to said body than to said actuator;
wherein
said actuator includes a reaming element mounting portion for mounting said reaming element thereto, said reaming element mounting portion including a radially central portion and an arm extending outwardly from said radially central portion, said reaming element being mounted to said arm; and
said reaming element lock includes two locking components each mounted to said body so as to be movable between a respective locked position and a respective unlocked position, said reaming element lock being in said locked configuration when said locking components are in said respective locked positions and said reaming element lock being in said unlocked configuration when said locking components are in said respective unlocked positions, said two locking components being circumferentially spaced apart from each other and defining a circumferentially extending gap therebetween, said reaming element being partially inserted in said gap, said locking components frictionally engaging said reaming element when said locking components are in said locked position.

13. An acetabular reamer as defined in claim 12, wherein said two locking components each define a respective groove for slidably mounting said reaming element thereto and guiding said reaming element therealong when said reaming element is moved between said reaming element inner and outer positions.

14. An acetabular reamer as defined in claim 12, wherein said reaming element lock includes a lock actuating element operatively coupled to said two locking components for configuring said reaming element lock between said locked and unlocked configurations.

15. An acetabular reamer as defined in claim 14, wherein said two locking components are mounted to said body so as to be movable radially relatively to said rotation axis; said two locking components each define a respective locking component actuating portion;
said lock actuating element includes a sleeve mounted to said body so as to be longitudinally movable therealong, said sleeve defining a locking component mounting passageway extending longitudinally, said locking component actuating portion of said two locking components being at least partially located in said locking component mounting passageway, said locking component mounting passageway engaging said two locking components in a manner such that said two locking components are moved between said locking component locked and unlocked positions when said sleeve is moved longitudinally along said body.

16. An acetabular reamer as defined in claim 15, wherein said locking component actuating portions each define a respective actuating portion radially outwardmost surface, said respective actuating portion radially outwardmost surface being shaped similarly to an arc segment of a frustrum of a cone;

said locking component mounting passageway is frusto-conical;

said locking component mounting passageway and said actuating portion radially outwardmost surfaces are parallel to each other.

17. An acetabular reamer as defined in claim 12, wherein said acetabular reamer is usable with a rotary power tool, said body defining a power tool attachment for attaching said acetabular reamer to said rotary power tool so that said body is rotatable thereby about said rotation axis.

* * * * *